(12) United States Patent
Tajima

(10) Patent No.: US 11,313,871 B2
(45) Date of Patent: Apr. 26, 2022

(54) SPECIMEN TREATMENT AND MEASUREMENT SYSTEM

(71) Applicant: UNIVERSAL BIO RESEARCH CO., LTD., Chiba (JP)

(72) Inventor: Hideji Tajima, Chiba (JP)

(73) Assignee: UNIVERSAL BIO RESEARCH CO., LTD., Chiba (JP)

( * ) Notice: Subject to any disclaimer, the term of this patent is extended or adjusted under 35 U.S.C. 154(b) by 252 days.

(21) Appl. No.: 16/497,843

(22) PCT Filed: Mar. 28, 2018

(86) PCT No.: PCT/JP2018/012791
§ 371 (c)(1),
(2) Date: Sep. 26, 2019

(87) PCT Pub. No.: WO2018/181487
PCT Pub. Date: Oct. 4, 2018

(65) Prior Publication Data
US 2020/0033372 A1    Jan. 30, 2020

(30) Foreign Application Priority Data

Mar. 29, 2017   (JP) ............................. JP2017-064984
Jul. 14, 2017   (JP) ............................. JP2017-137707

(51) Int. Cl.
     *G01N 35/04*    (2006.01)
     *G01N 35/00*    (2006.01)
     *B01L 3/00*    (2006.01)

(52) U.S. Cl.
CPC .......... *G01N 35/04* (2013.01); *B01L 3/50855* (2013.01); *G01N 35/00732* (2013.01);
(Continued)

(58) Field of Classification Search
CPC ............. G01N 35/04; G01N 35/00732; G01N 2035/00801; G01N 2035/0401
See application file for complete search history.

(56) References Cited

U.S. PATENT DOCUMENTS

| 6,509,193 B1 | 1/2003 | Tajima |
| 2004/0248087 A1 | 12/2004 | Burg et al. |

(Continued)

FOREIGN PATENT DOCUMENTS

| EP | 2439537 A1 | 4/2012 |
| EP | 3441747 A1 | 2/2019 |

(Continued)

OTHER PUBLICATIONS

Partial supplementary European Search Report in connection to Application No. 18774187.1, dated Dec. 3, 2020.
(Continued)

*Primary Examiner* — Benjamin R Whatley
(74) *Attorney, Agent, or Firm* — Meunier Carlin & Curfman LLC

(57) ABSTRACT

The specimen treatment and measurement system 2000 according to the present invention is provided with: a movement stage 2300 having a plurality of treatment lanes for treating specimens in parallel; a consumables supply module 2100 for storing consumables for use in treatment of the specimens, and supplying the consumables to the movement stage 2300; a cartridge supply module 2500 for storing cartridges for use in treatment of the specimens, and supplying the cartridges to the movement stage 2300; and a stage transfer mechanism 2400 for transferring the movement stage 2400 to each module. The cartridge supply module 2500 has a plurality of cartridge cartons for accommodating the cartridges stacked on top of each other, and a push-out mechanism for pushing cartridges out of a car- (Continued)

tridge carton to a supply position of the cartridge supply module 2500.

11 Claims, 35 Drawing Sheets

(52) U.S. Cl.
CPC .............. *G01N 2035/00326* (2013.01); *G01N 2035/00801* (2013.01); *G01N 2035/0401* (2013.01); *G01N 2035/0415* (2013.01); *G01N 2035/0425* (2013.01)

(56) References Cited

U.S. PATENT DOCUMENTS

| | | |
|---|---|---|
| 2009/0130745 A1 | 5/2009 | Williams et al. |
| 2009/0305392 A1 | 12/2009 | Alfredsson et al. |
| 2011/0262919 A1 | 10/2011 | Tajima |
| 2012/0269604 A1 | 10/2012 | Baumann et al. |
| 2013/0130369 A1 | 5/2013 | Wilson et al. |
| 2014/0329301 A1 | 11/2014 | Handique |
| 2015/0323776 A1* | 11/2015 | Dyson-Holland ..... G01N 1/312 348/79 |
| 2017/0115476 A1* | 4/2017 | Ewoniuk ................ G02B 21/34 |
| 2018/0284146 A1* | 10/2018 | Hansen .................. G01N 35/04 |

FOREIGN PATENT DOCUMENTS

| | | |
|---|---|---|
| EP | 3467512 A1 | 4/2019 |
| GB | 2532780 A | 6/2016 |
| JP | S60-055263 A | 3/1985 |
| JP | S62-030962 A | 2/1987 |
| JP | S6230962 B2 * | 7/1987 |
| JP | 11-304812 | 11/1999 |
| JP | 2008-14638 | 1/2008 |

OTHER PUBLICATIONS

Extended European Search Report, in connection to EP Application No. 18774187.1, dated Apr. 6, 2021.
Written Opinion of the International Searching Authority of PCT/JP2018/012791, dated Jul. 3, 2018.

* cited by examiner (a)

(b)

SPECIMEN TREATMENT AND MEASUREMENT SYSTEM

TECHNICAL FIELD

The present invention relates to a specimen treatment and measurement system for continuously treating and measuring specimens of multiple types of biological substances. More particularly, the present invention relates to a specimen treatment and measurement system which can efficiently provide cartridges that are used for treating and measuring specimens.

BACKGROUND ART

Samples of biological substances such as genes are subjected to a predetermined pretreatment prior to a measurement process such as detection or quantification. Such a predetermined pretreatment may be a physical treatment such as capture, purification, separation, washing or the like of the samples, gene amplification, a chemical reaction treatment, or the like. The measurement process may be measurement of chemiluminescence, fluorescence, absorbance or the like. In order to carry out such pretreatment and measurement, plastic parts or consumables like dispenser chips for dispensing multiple reagents, reaction solutions or the like need to be selected according to the purpose of the treatment, and sequentially used to perform an appropriate pretreatment step.

The present inventor has proposed Magtration technology that utilizes magnetic particles (Patent document 1). Besides Magtration technology, the present inventor further made a multiple-specimen collective batch treatment possible by controlling dispensation such that dispensation of a solution is controlled and magnetic bodies are separated at the same time by using an alignment of multiple cartridges and a plurality of dispenser nozzles as proposed in Patent document 2.

For automation of the pretreatment, two modes, namely, a multiple-sample batch mode and a one-sample random-access mode have been proposed. In the multiple-sample batch mode, multiple samples are collectively treated in parallel. An example of a product employing the multiple-sample batch mode includes "geneLEAD XII" provided by Precision System Science Co., Ltd. Examples of products employing the multiple-sample batch mode include the "cobas" series provided by Roche Diagnostics Inc. In the one-sample random-access mode, information of each sample is read one by one so that separate physical and reaction treatments are sequentially performed based on the information.

PRIOR ART DOCUMENTS

Patent Documents

Patent document 1: Japanese Patent No. 3682302 (FIG. 3)
Patent document 2: International Patent Application Publication WO2010/074265 (FIG. 38)

SUMMARY OF INVENTION

Problem to be Solved by Invention

The benefit of the multiple-sample batch mode is that the apparatus can be downsized and simplified by collectively treating multiple samples by having "a system configuration in which functional sections that are employed for the treatments are fixed". The drawback of the multiple-sample batch mode, however, is the difficulty in dealing with samples that require different kinds of steps and in dealing with continuously introduced different kinds of samples. Specifically, suppose that multiple samples $S_{A1}$, $S_{A2}$, $S_{A2}$, $S_{A3}$, $S_{A4}$, $S_{A5}$, $S_{A6}$, $S_{AB1}$ and $S_{BC1}$ are to be treated employing the multiple-sample batch mode as shown in FIG. 1. Samples $S_{A1}$, $S_{A2}$, $S_{A2}$, $S_{A3}$, $S_{A4}$, $S_{A5}$ and $S_{A6}$ require a pretreatment of Item A and do not require pretreatments of Items B and C. Sample $S_{AB1}$ requires sequential pretreatments of Items A and B but does not require the pretreatment of Item C. Sample $S_{BC1}$ requires sequential pretreatments of Items B and C but does not require the pretreatment of Item A. When multiple samples require different items like this, it is difficult to simultaneously treat the multiple samples in parallel by a multiple-sample batch treatment.

On the other hand, the benefit of the one-sample random-access mode is that samples that require multiple step treatments (items) can continuously and consistently be treated for different treatment items. The drawback of the one-sample random-access mode, however, is that the samples need to be transferred from one functional section to another functional section designated for the treatments so as to execute different treatment steps as shown in FIG. 2. Accordingly, the hardware and the software for controlling the treatment steps become complicated because the treatment steps differ for each sample. As a result, it has a problem that the required system or apparatus has to be very complicated, expensive and large (5-10 m). For example, suppose that Samples $S_{A1}$, $S_{AB1}$ and $S_{BC1}$ are to be treated by the one-sample random-access mode as shown in FIG. 2. First, Sample $S_{A1}$ is transferred to the Item A treatment functional section to execute the treatment step for Item A, and thereafter Sample $S_{A1}$ is transferred to the sample recovering section. Next, Sample $S_{AB1}$ is transferred to the Item A treatment functional section to execute the treatment step for Item A, then Sample $S_{AB1}$ is transferred to the Item B treatment functional section to execute the treatment step for Item B, and Sample $S_{AB1}$ is transferred to the sample recovering section. Finally, Sample $S_{BC1}$ is transferred to the Item B treatment functional section to execute the treatment step for Item B, then Sample SBC1 is transferred to the Item C treatment functional section to execute the treatment step for Item C, and Sample $S_{BC1}$ is transferred to the sample recovering section. Moreover, since the one-sample random-access mode treats the samples one by one, there is also a problem that it takes a long time to treat multiple samples.

Requirements for an automation system for the steps of pretreating multiple samples are as follows. Since there are several tens of kinds of test items required, an information management system is required for accurately selecting reagents and consumables via barcodes and IC tags without making a mistake. In addition, there is a need to consider a stage layout and a transfer method that can realize prevention of contamination such that not even a trace amount of the reagent or sample gets mixed, and that can realize housing, supplying and discarding the reagents and the consumables so that samples can be continuously treated as much as possible. Besides, there are issues of an interrupt function for giving priority to a specimen for emergent testing during the continuous treatments of multiple samples, a user-friendly interface for easy operation by the operator, size reduction of the main body of the apparatus, affordable price, and a structure that ensures safety.

The present invention has an objective of providing a novel specimen treatment and measurement system which is capable of continuously treating and measuring multiple specimens in an efficient manner. Alternatively, the present invention has an objective of providing a novel specimen treatment and measurement system which is capable of efficiently storing, taking out, loading and/or discarding a plurality of cartridges that are used for treating multiple specimens.

Means for Solving Problem

Each aspect of the present invention is as follows.

(Aspect 1) A specimen treatment and measurement system for executing treatments including extraction, amplification and measurement of nucleic acids for multiple specimens in parallel, the system comprising: a movable stage provided with a plurality of treatment lanes for executing the treatments in parallel; a treatment execution module for executing the treatments by loading the movable stage therein; and a consumable supply module for supplying specimens and consumables used for the treatments to the movable stage, wherein the movable stage is detachable or exchangeable with respect to the treatment execution module while one or a plurality of cartridges are installed in the plurality of treatment lanes. (Aspect 2) The specimen treatment and measurement system according to Aspect 1, wherein the treatment is a batch treatment that is performed for the multiple specimens at the same time. (Aspect 3) The specimen treatment and measurement system according to either one of Aspects 1 and 2, wherein at least a part of the cartridge includes a prefilled well in which a reagent and/or a solution required for the treatment is sealed in advance.

(Aspect 4) The specimen treatment and measurement system according to any one of Aspects 1-3, wherein: the specimen treatment and measurement system comprises a plurality of treatment execution modules; and the consumable supply module is arranged between the plurality of treatment execution modules. (Aspect 5) The specimen treatment and measurement system according to any one of Aspects 1-4, the system comprising a pick-up unit for supplying the multiple specimens and/or the consumables from the consumable supply module to the movable stage. (Aspect 6) The specimen treatment and measurement system according to Aspect 5, the system comprising a pick-up unit moving mechanism for moving the pick-up unit above the treatment execution module and the consumable supply module. (Aspect 7) The specimen treatment and measurement system according to any one of Aspects 1-3, the system further comprising: a cartridge supply module for storing cartridges that are used for at least one of extraction, amplification and measurement and supplying the cartridges to the movable stage; and a stage transfer mechanism for transferring the movable stage to each module.

(Aspect 8) The specimen treatment and measurement system according to Aspect 7, wherein the cartridge supply module comprises at least one cartridge storage container for storing the cartridges in a stack, and a cartridge supplying mechanism for supplying the cartridges from the cartridge storage container to a supply position in the cartridge supply module. (Aspect 9) The specimen treatment and measurement system according to Aspect 8: wherein the cartridge supplying mechanism comprises a push-out bar for pushing out the cartridges from the cartridge storage container to the supply position; and the cartridge storage container comprises a bar insertion opening for inserting the push-out bar into the cartridge storage container and a push-out opening for pushing out the cartridges from the cartridge storage container to the supply position. (Aspect 10) The specimen treatment and measurement system according to either one of Aspects 8 and 9, wherein the cartridge supplying mechanism supplies the cartridge in the bottommost row of the cartridges stacked in the cartridge storage container to the supply position.

(Aspect 11) The specimen treatment and measurement system according to any one of Aspects 8-10, wherein the cartridge storage container and/or the cartridges comprise an information storage medium for readably storing the information of the cartridges. (Aspect 12) The specimen treatment and measurement system according to Aspect 11, wherein the cartridge supply module comprises an information reading unit for reading cartridge information from the information storage medium. (Aspect 13) The specimen treatment and measurement system according to any one of Aspects 8-12, further comprising an accommodating shelf having a plurality of shelves for accommodating a plurality of cartridge storage containers. (Aspect 14) The specimen treatment and measurement system according to Aspect 13, the system comprising a shelf moving mechanism for moving the plurality of shelves with respect to the supply position of the cartridges. (Aspect 15) The specimen treatment and measurement system according to any one of Aspects 7-14, wherein the cartridge supply module comprises a cartridge picker for picking up and moving at least one cartridge.

(Aspect 16) The specimen treatment and measurement system according to Aspect 15, wherein the cartridge picker comprises a suction part for suctioning the cartridge. (Aspect 17) The specimen treatment and measurement system according to either one of Aspects 15 and 16, wherein the cartridge picker comprises a plurality of suction parts for suctioning the cartridges. (Aspect 18) The specimen treatment and measurement system according to Aspect 17, wherein the cartridge picker comprises a ranging mechanism for ranging the distance between the pair of suction parts in accordance with the plurality of cartridges having different longitudinal dimensions. (Aspect 19) The specimen treatment and measurement system according to Aspect 17, wherein the cartridge picker comprises a plurality of pairs of suction parts spaced at different distances in accordance with the plurality of cartridges having different longitudinal dimensions.

(Aspect 20) The specimen treatment and measurement system according to any one of Aspects 15-19, wherein the cartridge picker comprises a projection while the cartridge comprises a recess into which the projection can be inserted. (Aspect 21) The specimen treatment and measurement system according to any one of Aspects 15-20, wherein the cartridge picker comprises a cartridge picker elevating mechanism for raising/lowering the cartridge picker. (Aspect 22) The specimen treatment and measurement system according to any of Aspects 1-21, the system comprising a cartridge securing mechanism for securing the cartridge to the movable stage. (Aspect 23) The specimen treatment and measurement system according to any one of Aspects 1-22, the system comprising an extract storage section for fractionating and storing a part of an extract obtained by the nucleic acid extraction in the treatment execution module.

(Aspect 24) The specimen treatment and measurement system according to Aspect 23, wherein the extract storage section is provided in the consumable supply module. (Aspect 25) The specimen treatment and measurement system according to any one of Aspects 1-24, wherein once an extract is obtained by the nucleic acid extraction in the treatment execution module, a part of the extract is fractionated from a first treatment lane and dividedly transferred to one or a plurality of second treatment lanes. (Aspect 26) The specimen treatment and measurement system according to Aspect 25, wherein the divided transfer is carried out by transferring the movable stage to the consumable supply module. (Aspect 27) The specimen treatment and measurement system according to any one of Aspects 1-26, wherein the treatment execution module comprises a treatment execution unit having a plurality of dispenser nozzles for executing the treatments in parallel for the cartridges loaded in each of the plurality of treatment lanes.

(Aspect 28) The specimen treatment and measurement system according to Aspect 27, wherein: the treatment execution module comprises a consumable discard section in which the consumables are discarded; and the dispenser nozzles of the treatment execution unit take out the consumables from the movable stage and discard the consumables in the consumable discard section during or after the treatments. (Aspect 29) The specimen treatment and measurement system according to either one of Aspects 27 and 28, wherein: the treatment execution module comprises a waste liquid tank in which a waste liquid containing the specimen is discarded; and the dispenser nozzles of the treatment execution unit suction the waste liquid from the movable stage and discard the waste liquid in the waste liquid tank during or after the treatments. (Aspect 30) The specimen treatment and measurement system according to any one of Aspects 15-21, wherein: the cartridge supply module comprises a cartridge discard section in which the cartridges are discarded; and the cartridge picker picks up a used cartridge to be discarded from the movable stage that has been transferred to the cartridge supply module and discards the cartridge in the cartridge discard section at the end of the pretreatment. (Aspect 31) The specimen treatment and measurement system according to Aspect 30, wherein the cartridge discard section comprises a discarded cartridge storage container for accommodating the discarded cartridge, and a cartridge aligning unit for aligning the discarded cartridges in the discarded cartridge storage container.

(Aspect 32) The specimen treatment and measurement system according to Aspect 31, wherein the cartridge aligning unit comprises an elevating arm that can be raised/lowered in the discarded cartridge storage container, and an elevating mechanism for the elevating arm. (Aspect 33) The specimen treatment and measurement system according to either one of Aspects 31 and 32, wherein the discarded cartridge storage container is the cartridge storage container that has been emptied. (Aspect 34) The specimen treatment and measurement system according to any one of Aspects 1-33, wherein at least a part of the cartridge comprises at least one prefilled well in which a solution used for the treatment, a reagent for extracting nucleic acids and/or a reagent for amplifying the nucleic acids is sealed in advance. (Aspect 35) The specimen treatment and measurement system according to any one of Aspects 1-34, wherein the movable stage comprises rails for slidably loading the cartridge, and a cartridge receiving port for guiding the cartridge to the rails. (Aspect 36) The specimen treatment and measurement system according to Aspect 35, wherein the movable stage comprises an upper surface body and a lower surface body including the rail, where the upper surface body and the rails limit the movement of the cartridge in the direction other than the sliding direction of the cartridge.

(Aspect 37) The specimen treatment and measurement system according to any one of Aspects 8-21, wherein: the movable stage comprises rails for slidably loading the cartridge and a cartridge receiving port for guiding the cartridge to the rails; and the cartridge receiving port of the movable stage is arranged at the supply position where the cartridge is supplied from the cartridge supply module. (Aspect 38) The specimen treatment and measurement system according to Aspect 37, wherein: the cartridge supply container comprises a cartridge supply port for supplying the cartridge to the supply position; and the cartridge receiving port of the movable stage opposes the cartridge supply port. (Aspect 39) The specimen treatment and measurement system according to either one of Aspects 37 and 38, wherein the cartridge supplying mechanism directly pushes the cartridge from the cartridge storage container onto the movable stage. (Aspect 40) The specimen treatment and measurement system according to any one of Aspects 1-39, where the cartridge comprises a first cartridge and a second cartridge, wherein the first cartridge and the second cartridge are accommodated in one lane.

Effect of the Invention

The specimen treatment and measurement system of the present invention is capable of efficiently executing continuous treatments to treat and measure multiple specimens that require different treatment steps. Furthermore, the specimen treatment and measurement system of the present invention is capable of efficiently storing, taking out, loading and/or discarding a plurality of cartridges that are used for treating multiple specimens.

MODES FOR CARRYING OUT INVENTION

Figure 1:
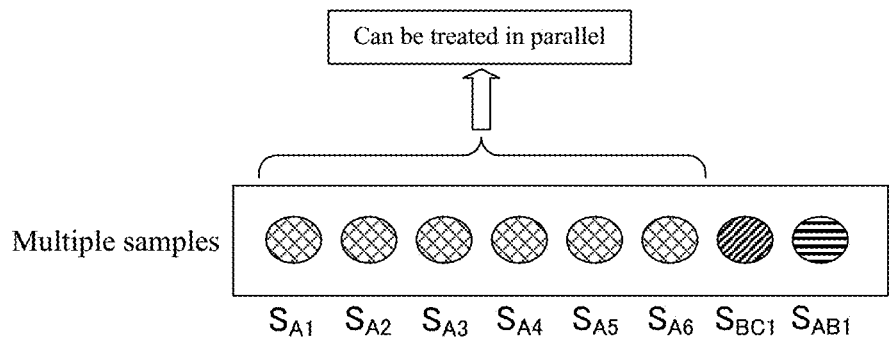
FIG. 1 A schematic view for illustrating a multiple-sample batch mode.
Figure 2:
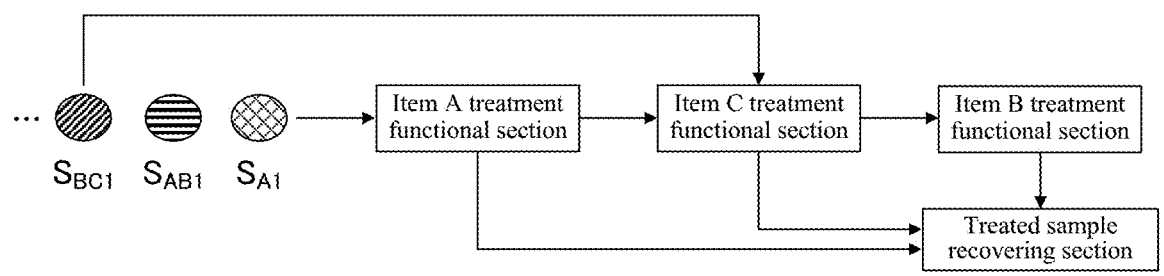
FIG. 2 A schematic view for illustrating one-sample random-access mode.
Figure 3:
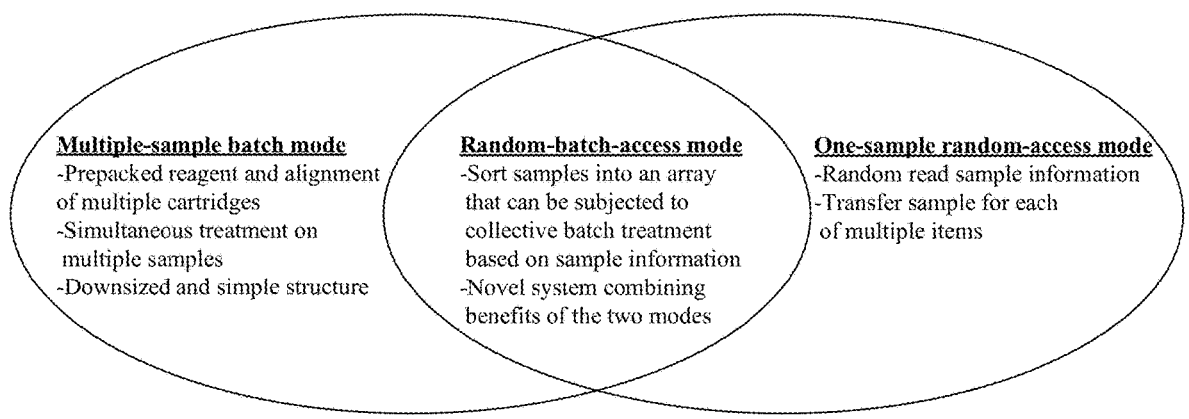
FIG. 3 A Venn diagram related to a random-batch-access mode of the present invention.

A specimen treatment and measurement system according to each embodiment of the present invention will be described with reference to the drawings. In the drawings, like reference numerals are used to denote like components. Note that relative size of each component is not completely consistent. Each embodiment of the present invention provides a specimen treatment and measurement system employing a random-batch-access mode, which is a combination of the conventional multiple-sample batch mode and one-sample random-access mode as shown in FIG. 3. The term "treatment" as used in each embodiment of the present invention comprises extraction, purification and amplification of specimens including nucleic acids, while the term "measurement" comprises measurements of the treated specimen (nucleic acids), for example, a measurement by real-time PCR or a measurement of bands by gel electrophoresis. In the description below, x-direction may represent be a substantially horizontal first direction, y-direction may represent a substantially horizontal second direction in a different direction from the first direction, and z-direction may represent a substantially vertical third direction.

[General Outline of Specimen Treatment and Measurement System According to First Embodiment]

A specimen treatment and measurement system 2000 according to the first embodiment of the present invention will be described. As can be appreciated from FIGS. 4 and 5, the specimen treatment and measurement system 2000 comprises a consumable supply module 2100, a treatment execution module 2200, a cartridge supply module 2500, a plurality of stage racks (movable stages) 2300 which can travel across the modules back and forth, a consumable supply module 2100, and a stage rack transferring mechanism 2400 for transferring the plurality of stage racks 2300 across the consumable supply module 2100, the treatment execution module 2200 and the cartridge supply module 2500. Consumables and the like are arranged or loaded on the stage racks 2300 in the consumable supply module 2100. The stage racks 2300 having the consumables and else arranged therein are transferred to the cartridge supply module 2500, where cartridges are loaded on the stage racks 2300. Alternatively, cartridges may be loaded on the stage racks 2300 in the cartridge supply module 2500, and then consumables and else may be loaded on the stage racks 2300 in the consumable supply module 2100. The stage racks 2300 loaded with the consumables and else and the cartridges are transferred to the treatment execution module 2200 to be installed into the treatment execution module 2200. The treatment execution module 2200 comprises a plurality of treatment execution units 400. These treatment execution units 400 parallelly execute treatments and measurements for multiple specimens accommodated in the specimen containers of the stage racks 2300 along a plurality of treatment lines provided on the stage racks 2300.

[Consumable Supply Module]

The consumable supply module 2100 comprises a consumable supply stage 2110 for storing various consumables and else, and a pick-up unit 300 which can move three-dimensionally above the consumable supply stage 2110. Furthermore, the consumable supply stage 2110 further comprises a consumable storage section 2140 for storing consumables such as dispenser chips and piercing chips, a container storage section 2150 for storing various reagent (PCR reagent, etc.) containers and/or secondary specimen containers, a primary specimen storage section 2160 for storing primary specimens, and a specimen extract storage section 2170. The consumable storage section 2140 may accommodate, for example, at least one or all of the consumables such as a large volume dispenser chip, a small volume dispenser chip and a piercing chip (piercer) for piercing aluminum seal of a sealed container. The container storage section 2150 accommodates, for example, at least one or all of the consumables such as a reaction solution well, a reagent well and caps for sealing PCR wells. The container storage section 2150, the primary specimen storage section 2160 and/or the specimen extract storage section 2170 preferably comprises a temperature control mechanism (cooling mechanism) for controlling (cooling) the temperatures of the reagents, the primary specimens and/or the specimen extracts. While the specimen extract storage section 2170 is provided in the consumable supply module 2100, the present invention is not limited thereto and the specimen extract storage section 2170 may be provided in other module. In this embodiment, the "consumables" are not limited to those stored in the consumable storage section 2140, and they also include those stored in the container storage section 2150, various reagents, solutions and specimens.

Figure 7:
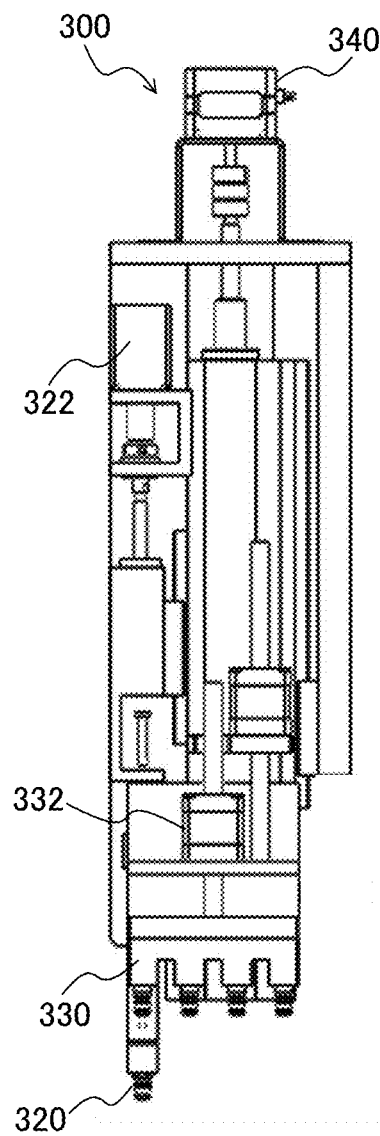
FIG. 7 A front view of a pick-up unit provided in the consumable supply module shown in FIG. 6.
Figure 8:
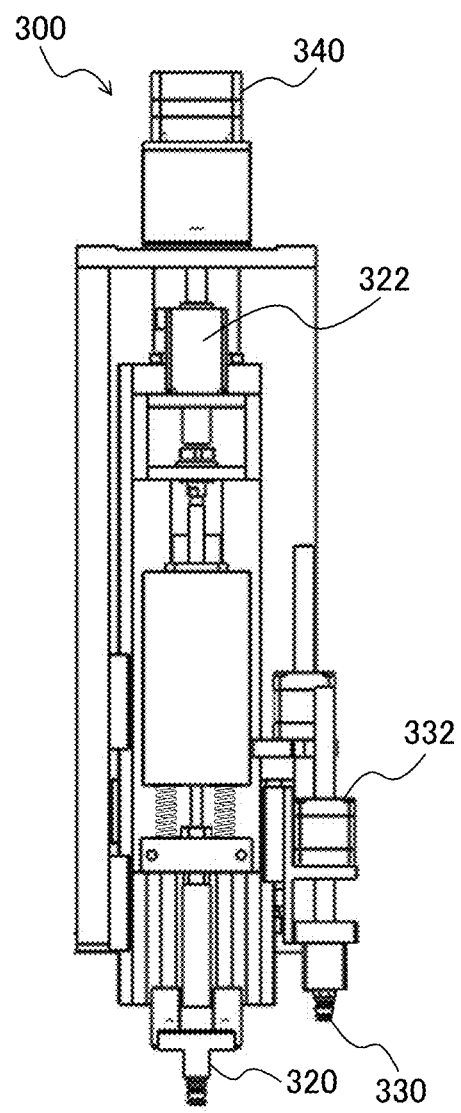
FIG. 8 A side view of the pick-up unit shown in FIG. 7.

As can be appreciated from FIGS. 7 and 8, the pick-up unit 300 comprises nozzle parts (dispenser nozzles) 320 to which the dispenser chips are connected, and a consumable picker (consumable detaching tool) 330 for picking up the consumables such as the dispenser chips, the tubes, the caps and the like. The nozzle part 320 can be raised/lowered by the nozzle part elevating motor 322 loaded in the pick-up unit 300. The nozzle part 320 with the dispenser chip attached thereto is capable of suctioning/discharging liquid into/from the dispenser chip with a vacuum pump (not shown). The consumable picker 330 can be raised/lowered by a consumable picker elevating motor 332 loaded in the pick-up unit 300. Moreover, the consumable picker 330 is formed as a multiple consumable picker having a plurality of joint ends (four joint ends in FIG. 7), where the plurality of joint ends can be joined with (inserted into) the openings of dispenser chips, tubes, caps and else so as to take them out all at once. Each joint end has a detaching tool (not shown) for detaching the picked up consumable therefrom by pushing it out or the like.

Figure 6:
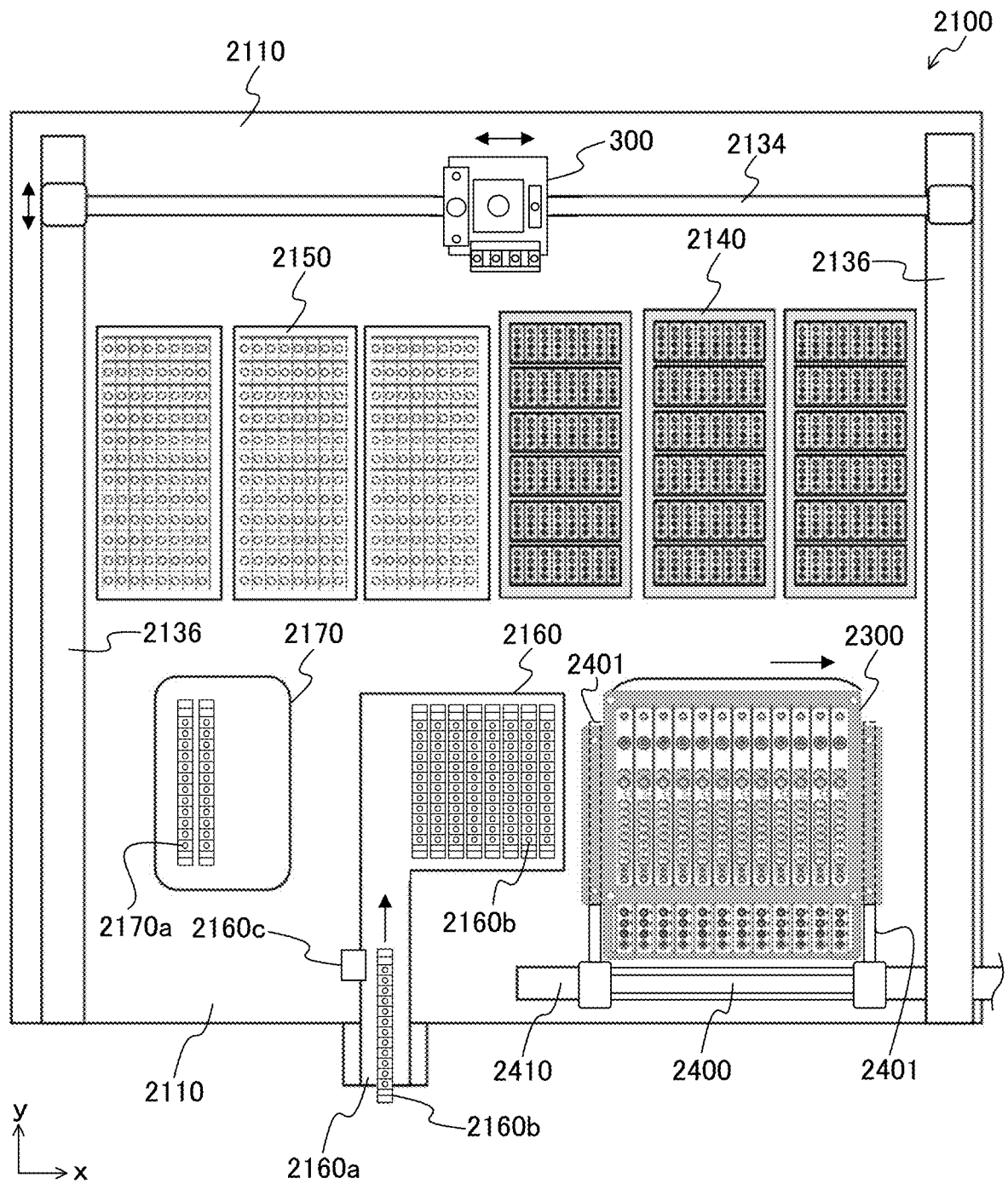
FIG. 6 A top view of a consumable supply module provided in the first embodiment of the present invention.

The primary specimen storage section 2160 shown in FIG. 6 stores multiple primary specimens (for example, vacuum blood collection tubes). The primary specimens are placed on a primary specimen tray 2160*b* and conveyed via the specimen inlet 2160*a*. The primary specimen tray (slim rack) 2160*b* preferably accommodates twelve primary specimen containers. Since the primary specimen storage section 2160 accommodates eight primary specimen trays 2160*b*, a total of 96 primary specimens can be accommodated. In addition, the surface of each primary specimen container is provided with an information storage medium such as a QR code (registered trademark), a barcode, an IC tag or the like. An information reader 2160*c* provided in the primary specimen storage section 2160 reads the specimen information from the information storage medium. The information storage medium stores any of specimen number, collection date of the specimen, place of collection (name of ward), doctor in charge, information of the patient who provided the specimen, whether or not it is an emergent specimen, infectious disease targeted by the test, or the like as the specimen information.

[Treatment Execution Module]

Figure 9:
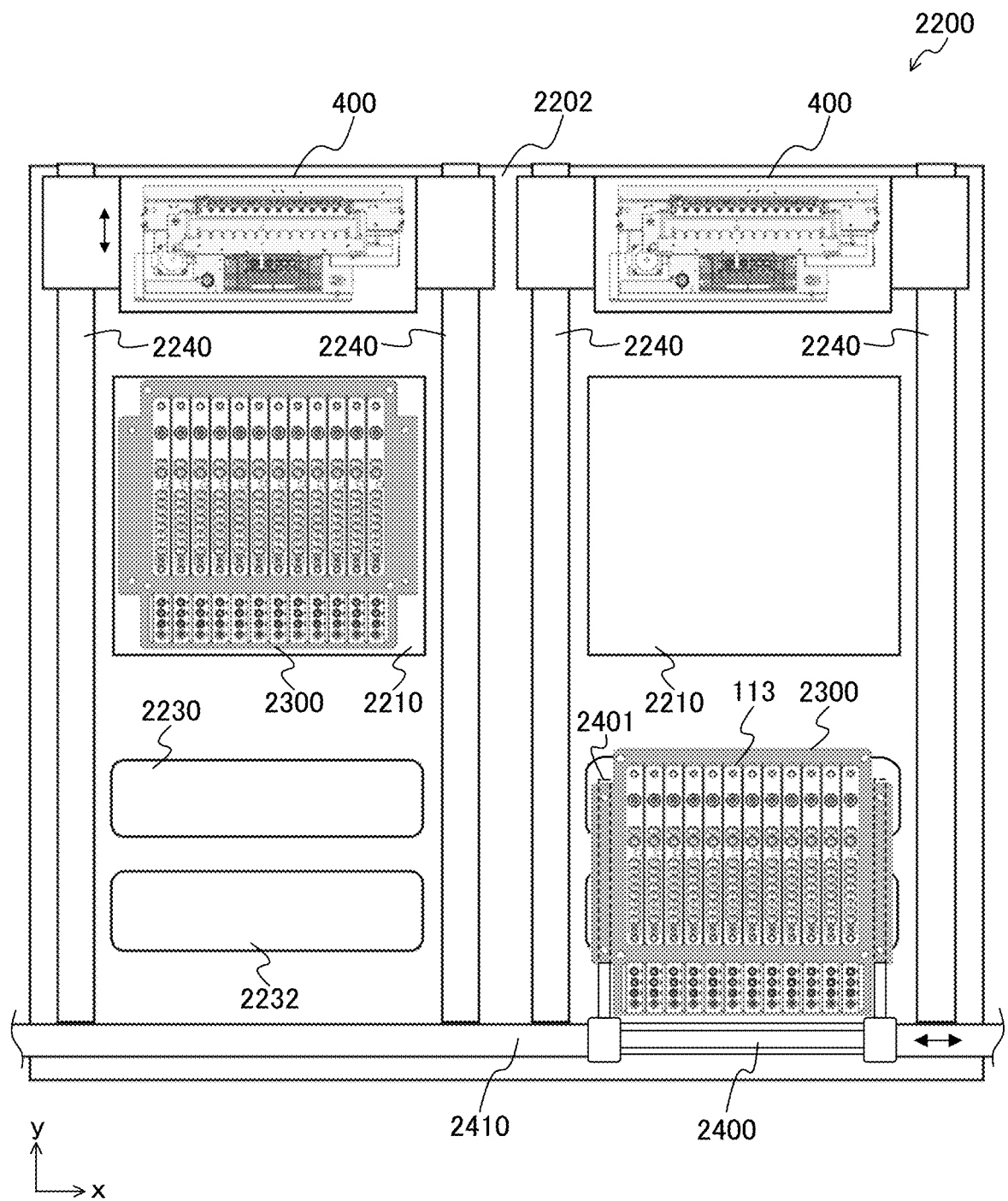
FIG. 9 A top view of a treatment execution module provided in the first embodiment of the present invention.

As can be appreciated from FIG. 9, the treatment execution module 2200 comprises a treatment/measurement stage 2202, a plurality of treatment execution units 400 provided on the treatment/measurement stage 2202, a stage rack installation section 2210 for installing the stage racks 2300 on each treatment/measurement stage 2202, and a stage rack installing mechanism 2250 for moving and installing the stage racks 2300 to the treatment/measurement stage 2202 (FIGS. 11-15). The plurality of treatment execution units 400 comprise a plurality of dispenser nozzles for treating and measuring the specimens, and they are independently movable back and forth in the y-direction along the rails 2240.

The treatment execution module 2200 comprises a consumable discard box 2230 and a waste liquid tank 2232 on the near side of the treatment/measurement stage 2202 and under the region where the stage racks 2300 move in the x-direction. The consumables (used dispenser chips, detached caps, and the like) which are detachable from the dispenser nozzles of the treatment execution units 400 are attached to the dispenser nozzles provided in the treatment execution units 400 while they are moved to arrive above the consumable discard box 2230. Subsequently, the consumables are detached (pushed out) from the dispenser nozzles by a consumable detaching mechanism provided on the dispenser nozzles to be discarded in the consumable discard box 2230. Similarly, waste liquids are suctioned into the dispenser nozzles of the treatment execution units 400 and moved to arrive above the waste liquid tank 2232. Subsequently, the waste liquids are discharged from the dispenser chips to be discarded in the waste liquid tank 2232.

[Stage Rack]

Figure 10:
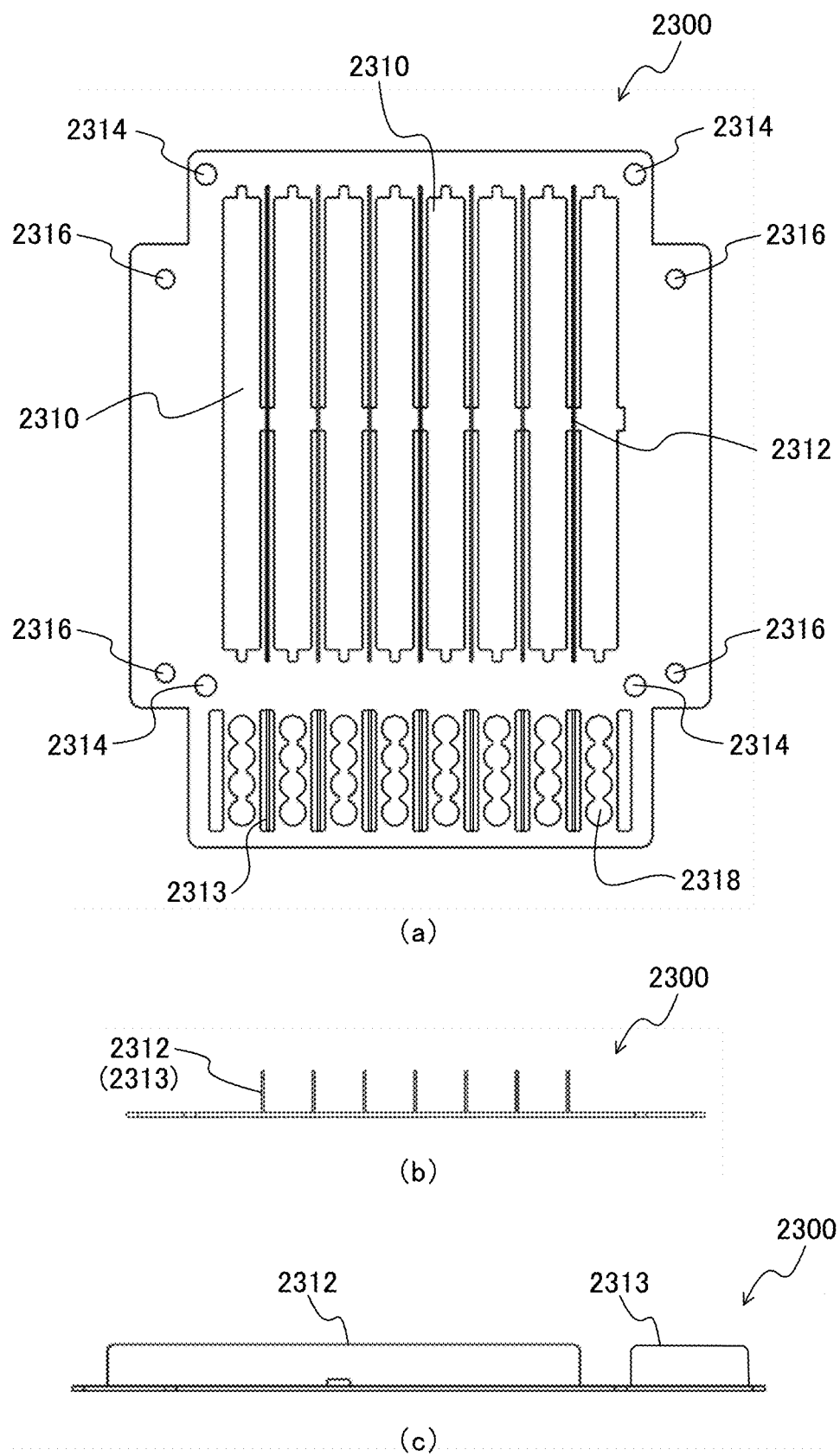
FIG. 10 (*a*) A top view, (*b*) a front view, and (*c*) a side view of a stage rack provided in the first embodiment of the present invention.

As can be appreciated from FIG. 10, the stage rack (movable stage) 2300 has a substantially flat plate, and comprises a plurality of parallelly arranged treatment lanes 2310 and tube accommodating slim parts 2318 corresponding to the respective treatment lanes. The pretreatment step (pretreatment function) and the measurement step (measurement function) are independently executed for each specimen in each of the treatment lanes. The position of a pretreatment functional section for executing the pretreatment step and the position of a measurement functional section for executing the measurement step are fixed in the treatment lane 2310. The tube accommodating parts 2318 accommodate one or more tubes for the secondary specimens and/or the reagents. Protruding partition walls 2312 are disposed between and parallel to the treatment lanes 2310. Protruding partition walls 2313 are disposed between and parallel to the tube accommodating parts 2318. The partition walls 2312 and 2313 can prevent contamination of the specimens treated in the respective treatment lanes.

Figure 11:
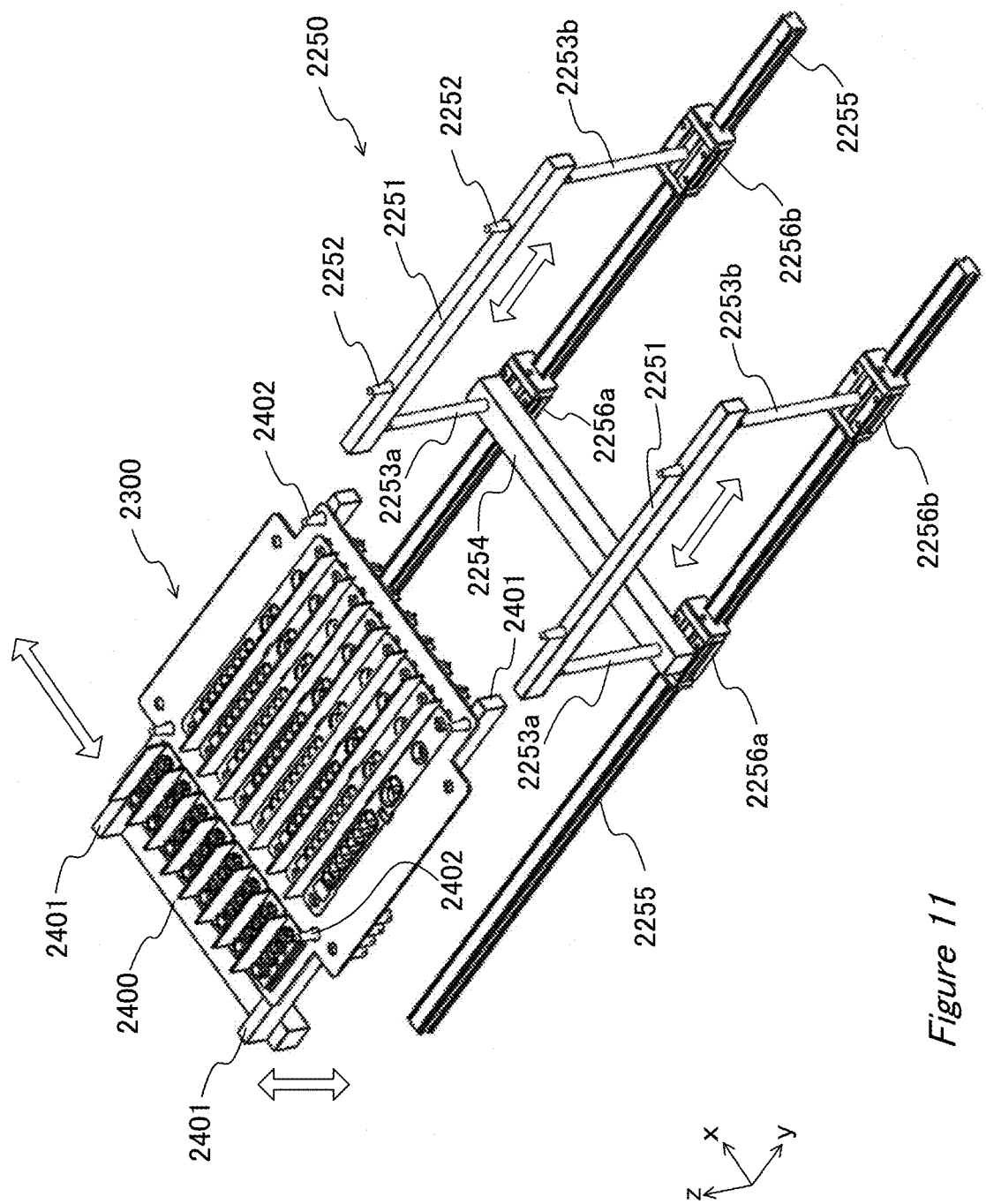
FIG. 11 A perspective view of a stage rack installing mechanism provided in the treatment execution module shown in FIG. 9.

The stage racks 2300 further comprises a plurality of connection holes for transfer 2314 and a plurality of connection holes for installation 2316. The plurality of connection holes for transfer 2314 are inserted with a plurality of protrusions for transfer 2402 of the stage rack transferring mechanism 2400 described later (FIGS. 11 and 14). The plurality of connection holes for installation 2316 are inserted with a plurality of protrusions for installation 2252 of the stage rack installing mechanism 2250 described later (FIGS. 11 and 14). The numbers of the connection holes for transfer 2314 and the connection holes for installation 2316 are preferably four each, but the number is not limited to four as long as the number is at least two or more. As can be appreciated from FIG. 13, a cartridge such as an integrated cartridge 113 in which a plurality of secondary specimen tubes, a DNA extraction cartridge and a PCR cartridge are integrated is disposed in each of the treatment lanes 2310. Although an integrated cartridge 113 is employed in this embodiment, the present invention is not limited thereto and a DNA extraction cartridge and a PCR cartridge may be disposed separately in a single treatment lane. These cartridges are each preferably molded from a transparent resin. Moreover, each of these cartridges may preferably be a prefilled cartridge that is provided with wells in which a lyophilized reagent, a solution or the like is sealed in advance. By doing so, operation for preparing a reagent or a solution bottle in advance and dispensing the content therefrom can be omitted.

As shown in FIG. 10, a single stage rack 2300 may preferably comprise eight treatment lanes 2310 and eight tube accommodating parts 2318 for treating eight different secondary specimens at the same time. Correspondingly, a single treatment execution unit 400 comprises eight dispenser nozzles, which simultaneously move along the respective treatment lanes and tube accommodating parts so as to perform treatment and measurement according to substantially the same protocol. The numbers of the treatment lanes 2310 and the tube accommodating parts 2318 provided on the stage rack 2300 are not limited to 8, and 4, 10, 12, 16 or any number of treatment lanes can be provided. Similarly, the number of the dispenser nozzles provided in the treatment execution unit 400 is also not limited to 8, and 4, 10, 12, 16 or any number of dispenser nozzles can be provided in correspondence with the number of the lanes provided in the stage rack.

[Stage Rack Transferring Mechanism]

Figure 4:
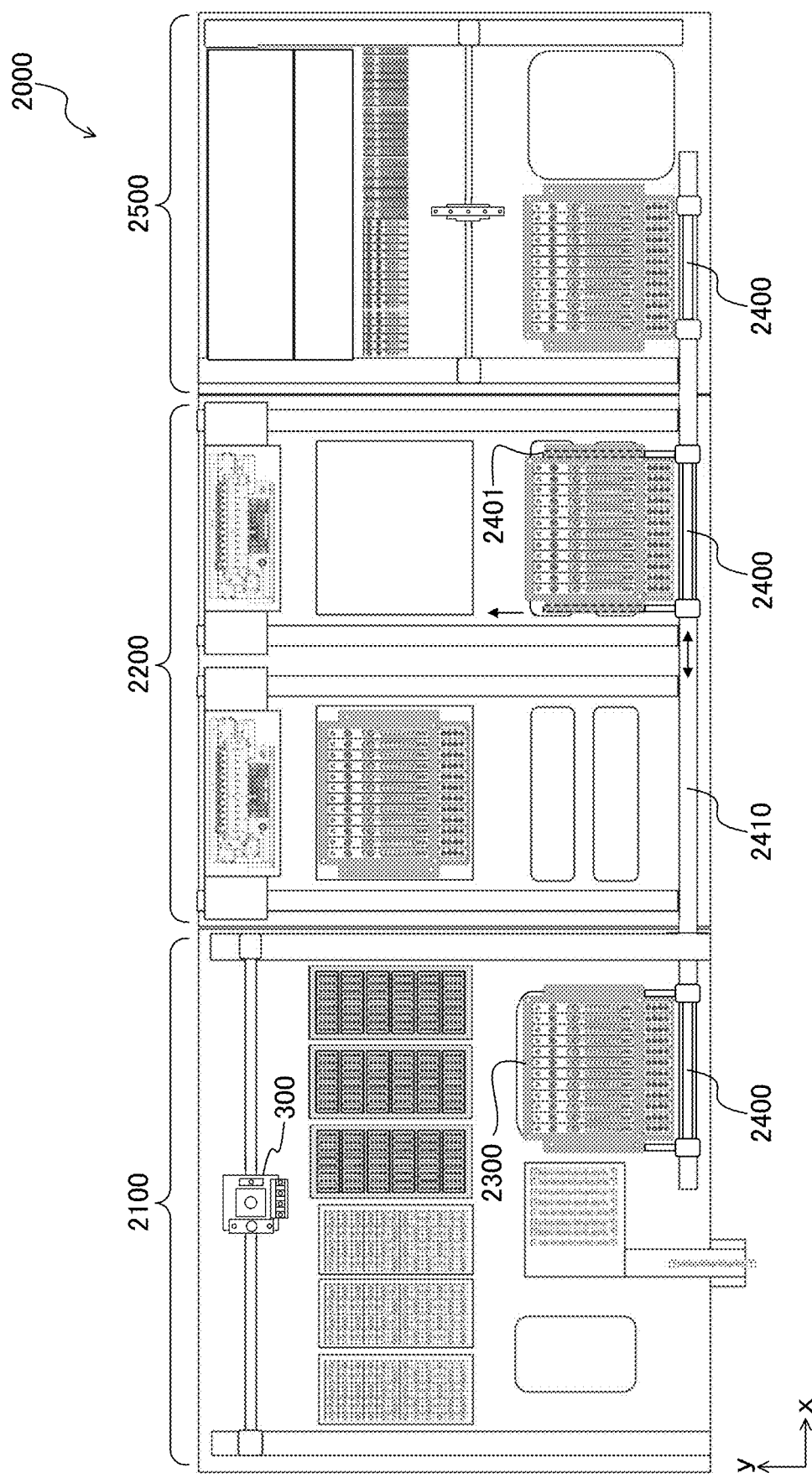
FIG. 4 A top view of a specimen treatment and measurement system according to a first embodiment of the present invention.
Figure 5:
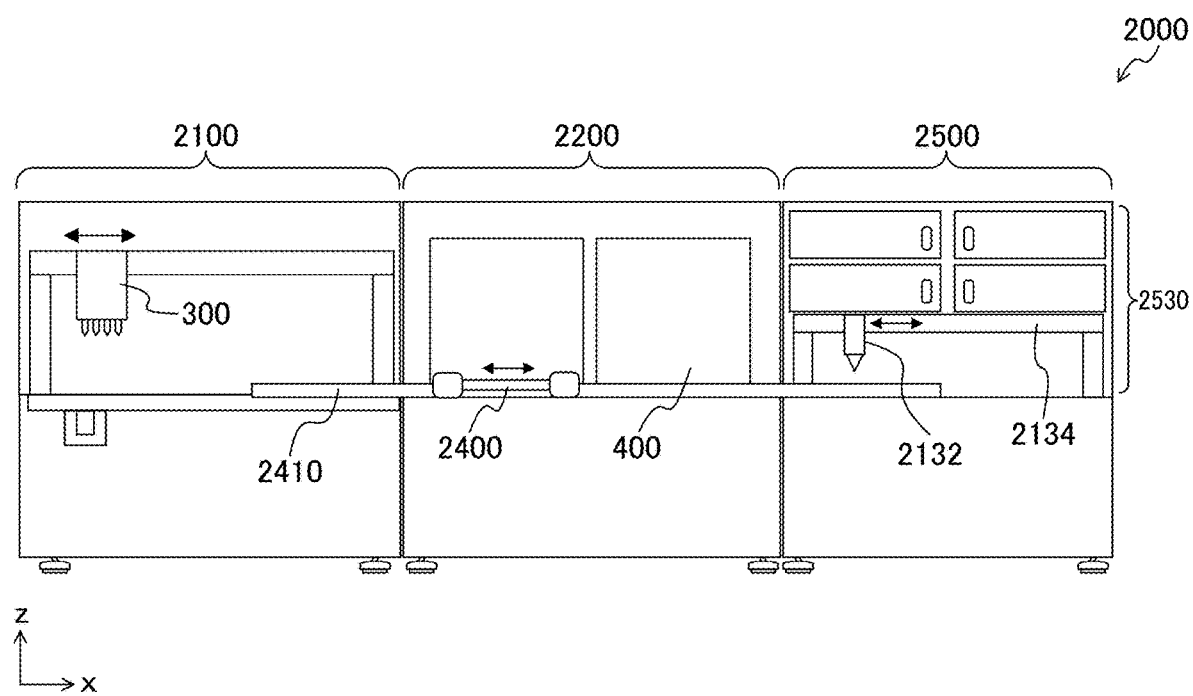
FIG. 5 A front view of the specimen treatment and measurement system shown in FIG. 4.

As can be appreciated from FIGS. 4 and 6, the stage rack transferring mechanism 2400 has a pair of stage rack transfer arms 2401. The stage rack transfer arms 2401 are movable back and forth along a rail 2410 extending across the consumable supply module 2100, the treatment execution module 2200 and the cartridge supply module 2500 by a transferring motor and slider (not shown). The upper surface of each of the stage rack transfer arms 2401 is provided with at least one protrusion for transfer 2402 (FIGS. 11 and 14). Once the protrusion for transfer 2402 is inserted into the connection hole for transfer 2314 of the stage rack 2300, the stage rack 2300 is secured to and integrated with the stage rack transferring mechanism 2400. As a result, the stage rack 2300 becomes movable back and forth along the rail 2410 while being held by the stage rack transfer arms 2401.

[Stage Rack Installing Mechanism]

The stage rack installing mechanism 2250 provided in the treatment execution module 2200 will be described with reference to FIG. 11. The stage rack installing mechanism 2250 is provided for each treatment execution unit 400 on the treatment/measurement stage 2202. The stage rack installing mechanism 2250 is provided on the treatment/measurement stage 2202 and is movable back and forth in the y-direction. The stage rack installing mechanism 2250 comprises a pair of stage rack installation arms 2251, at least one protrusion 2252 provided in each of the stage rack installation arms 2251, a pair of first columns 2253$a$ extending downward from one end of the respective stage rack installation arms 2251, a connection arm 2254 for connecting the lower ends of the pair of first columns 2253$a$, a pair of first sliders 2256$a$ provided at both ends of the connection arm 2254, second columns 2253$b$ extending downward from the other ends of the stage rack installation arms 2251, and second sliders 2256$b$ provided at lower ends of the second columns 2253$b$. In order to slide the first sliders 2256$a$ and the second sliders 2256$b$ in the y-direction, a pair of rails 2255 are provided on the stage 2240. Furthermore, the stage rack installing mechanism 2250 comprises a transferring motor (not shown) for automatically moving the stage rack installing mechanism 2250 back and forth.

Figure 12:
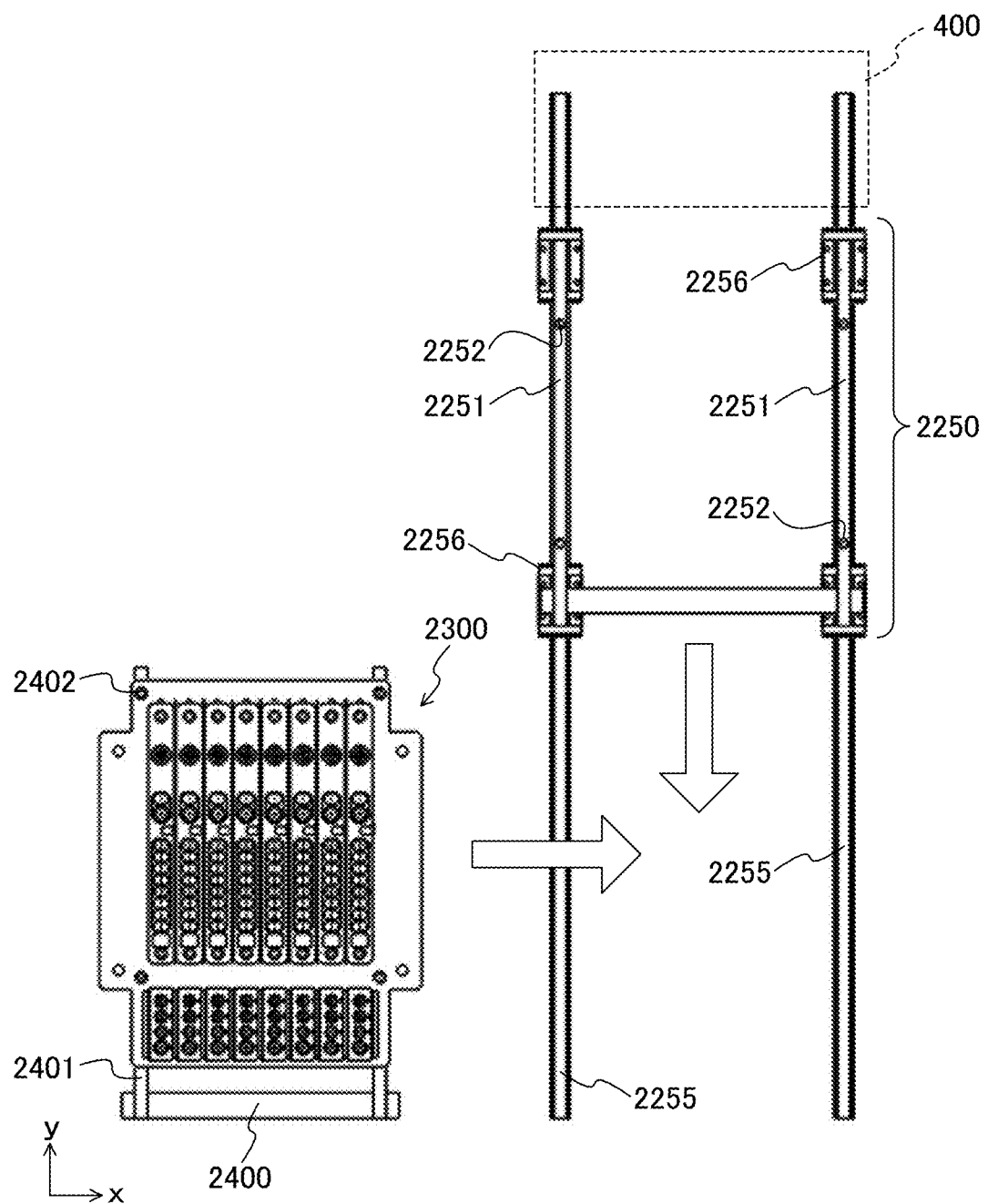
FIG. 12 A top view showing transfer of the stage rack to the stage rack installing mechanism shown in FIG. 11.

Next, transfer and installation of the stage rack 2300 using the stage rack transferring mechanism 2400 and the stage rack installing mechanism 2250 will be described with reference to FIGS. 12-15. The stage rack 2300 is held on the pair of stage rack transfer arms 2401 of the stage rack transferring mechanism 2400 while consumables and else are being loaded in each of the treatment lanes in the consumable supply module 2100, and cartridges such as cartridges 113 are further being loaded in the cartridge supply module 2500. Thereafter, the stage rack 2300 having the consumables and else and the cartridges loaded thereon moves from the consumable supply module 2100 or the cartridge supply module 2500 to the treatment execution module 2200 as shown in FIG. 12. The stage rack 2300 is further transferred above between the rails 2255 of the treatment execution module 2200 while the stage rack installing mechanism 2250 is moved below the stage rack 2300 as shown in FIG. 13.

Figure 13:
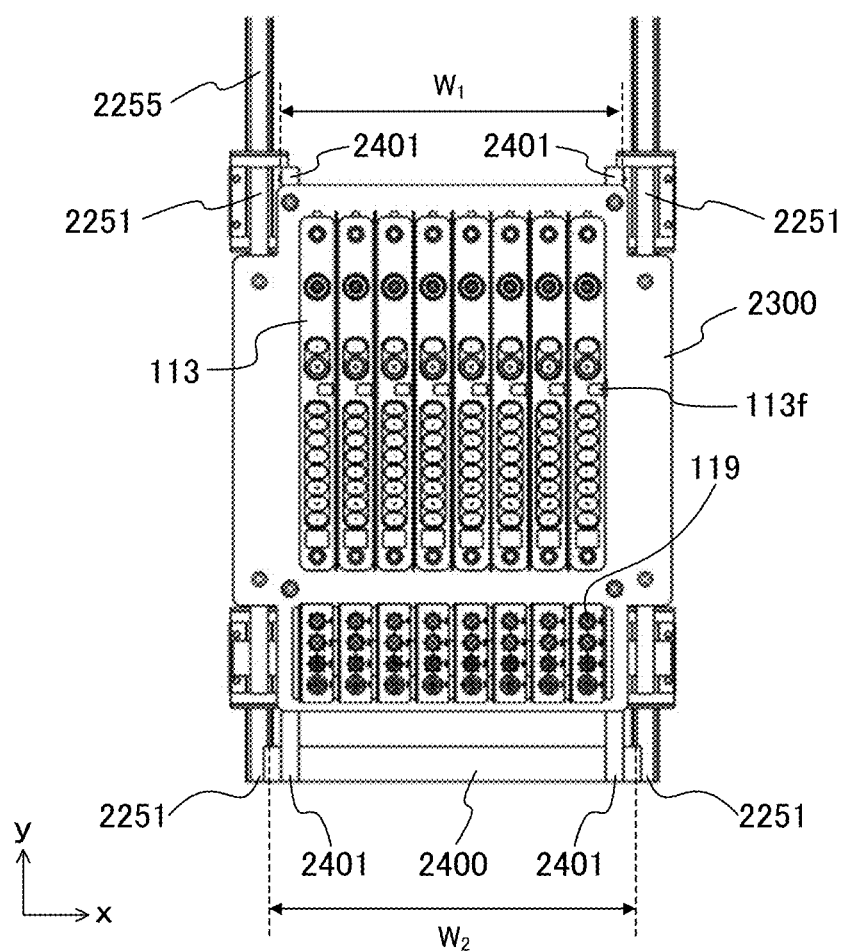
FIG. 13 A top view showing installation of the stage rack into the stage rack installing mechanism shown in FIG. 11.
Figure 14:
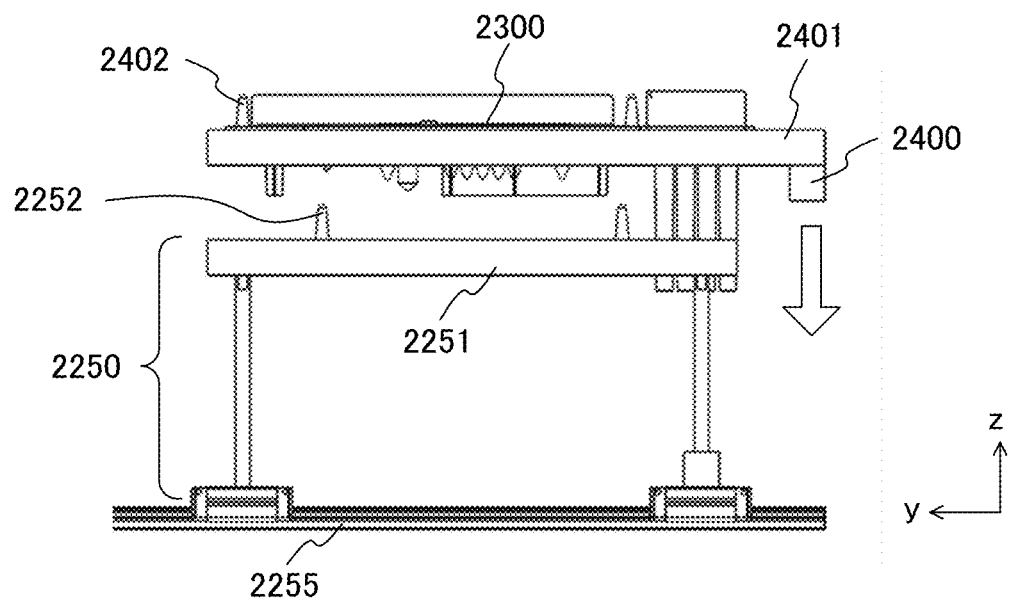
FIG. 14 A side view showing installation of the stage rack into the stage rack installing mechanism shown in FIG. 11.
Figure 14:
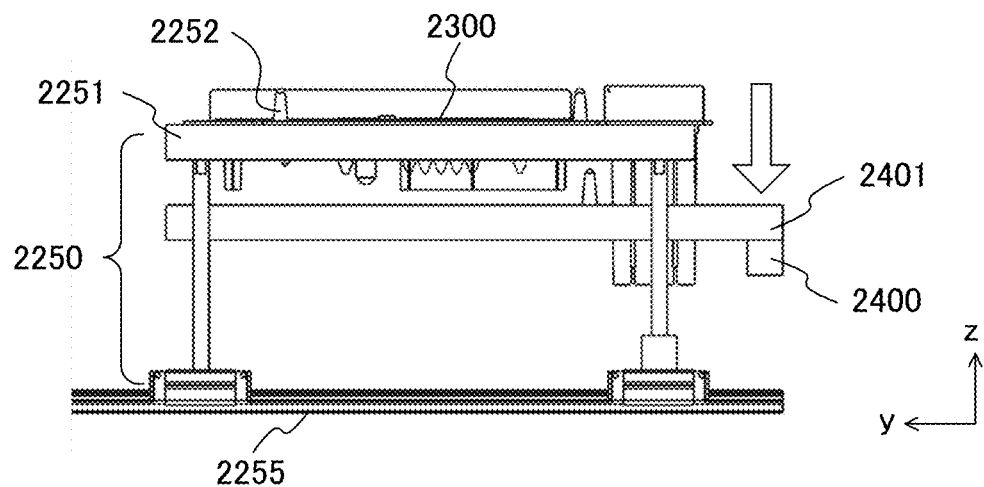
Figure 15:
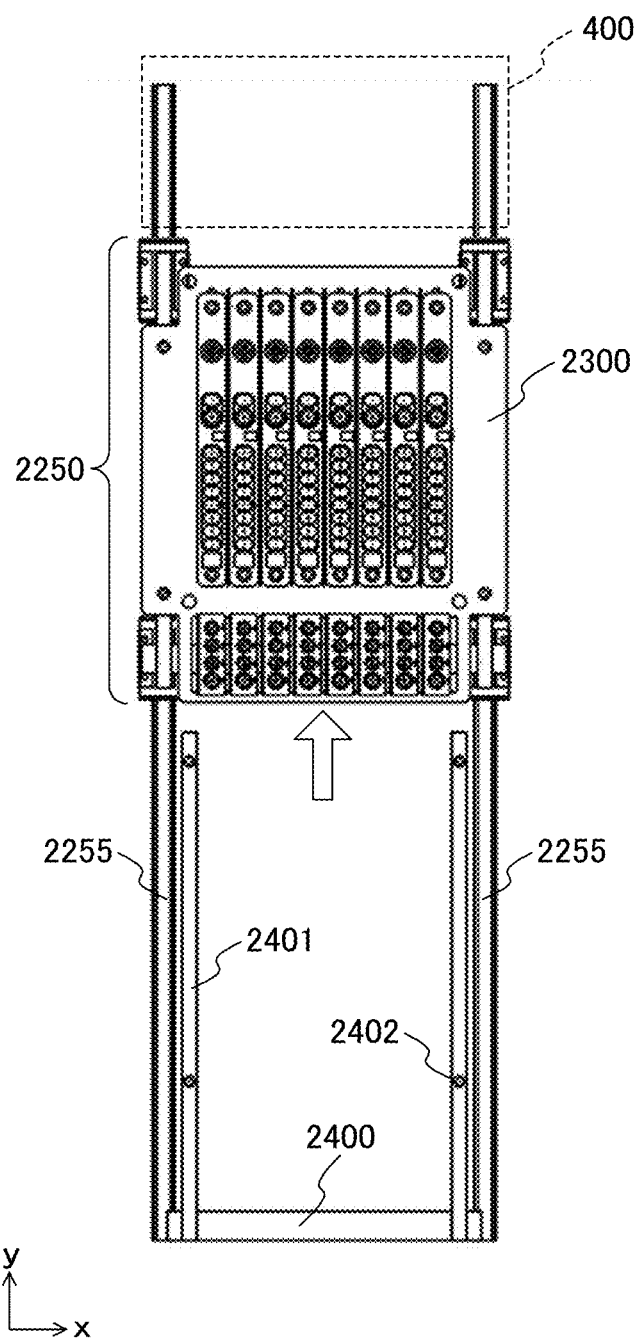
FIG. 15 A top view showing movement of the stage rack installed into the stage rack installing mechanism shown in FIG. 11.

FIG. 14 is a side view of the stage rack 2300 whose top view is shown in FIG. 13 seen in the x-direction. In FIG. 14($a$), the stage rack transferring mechanism 2400 holding the stage rack 2300 is positioned above the stage rack installing mechanism 2250. The stage rack transferring mechanism 2400 shown in FIG. 14($a$) is downwardly moved below the stage rack installation arms 2251 as shown in FIG. 14($b$) by an elevating mechanism (not shown). By this downward movement, the protrusions for transfer 2402 of the stage rack transfer arms 2401 are detached from the connection holes for transfer 2314 of the stage rack 2300, and the stage rack protrusions for installation 2252 of the stage rack installing mechanism 2250 are inserted into the connection holes for installation 2316 of the stage rack 2300. As a result, the stage racks 2300 is passed over from the stage rack transferring mechanism 2400 to the stage rack installing mechanism 2250. Since width $W_1$ between the outer sides of the pair of stage rack transfer arms 2401 is narrower than width $W_2$ between the inner sides of the pair of stage rack installation arms 2251 as shown in FIG. 13, the stage rack 2300 and the stage rack transfer arms 2401 do not interfere with each other upon this downward movement. Following the state shown in FIG. 14($b$), the stage rack installing mechanism 2250 holding the stage rack 2300 moves in the y-direction along the rails 2255, and stops at the stage rack installation section 2210 in front of the treatment execution unit 400 (installation position) as shown in FIG. 15, where treatments and measurements become possible.

[Cartridge Securing Mechanism]

Figure 16:
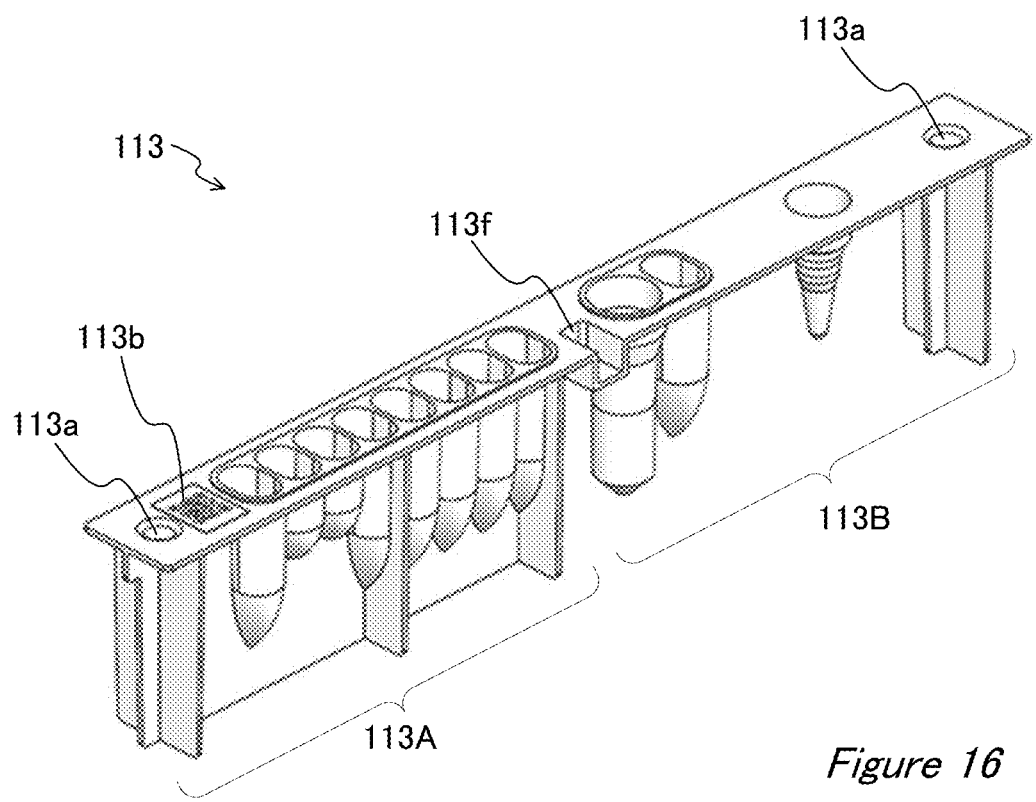
FIG. 16 A perspective view of a cartridge provided in the first embodiment of the present invention.
Figure 17:
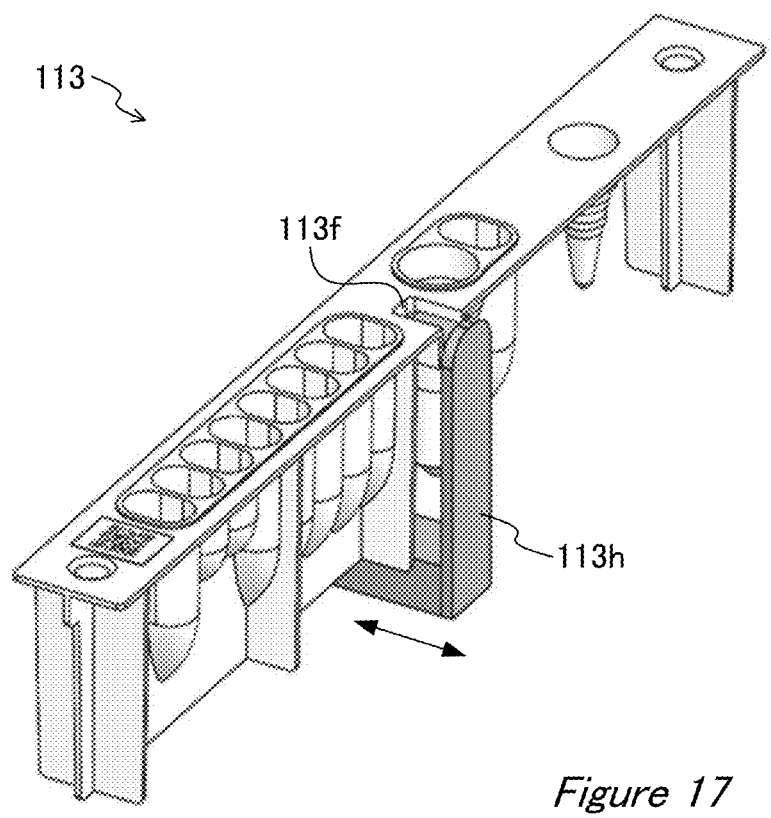
FIG. 17 A perspective view showing a securing mechanism for the cartridge shown in FIG. 16.
Figure 18:
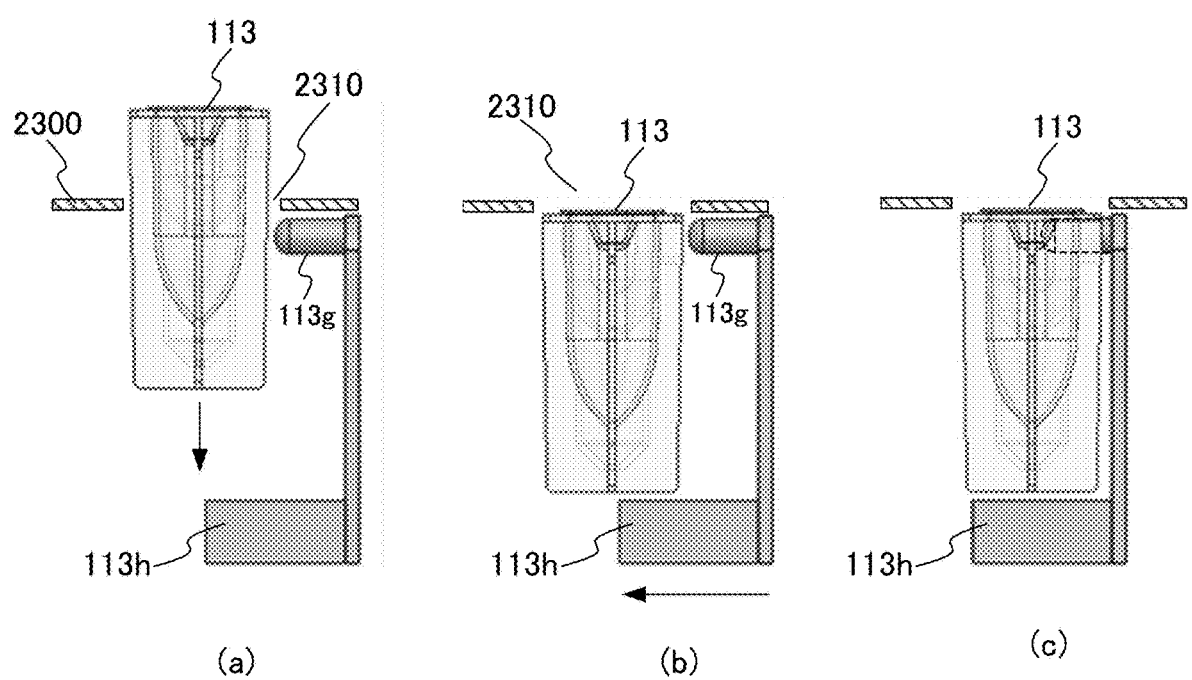
FIG. 18 A side view showing the operation of the securing mechanism for the cartridge shown in FIG. 17.

The cartridge securing mechanism for securing the integrated cartridge 113 or the like to the stage racks 2300 will be described with reference to FIGS. 16-18. As shown in FIG. 16, the integrated cartridge 113 is composed of a DNA extraction/purification section 133A and a PCR reaction measurement section 113B, which is an integration of an extraction cartridge and a PCR cartridge. The integrated cartridge 113 comprises a pair of hollows (a plurality of hollows) 113$a$ in the upper surface of the cartridge, an information storage medium 113$b$ for storing the type of the cartridge and the like, and a plurality of wells. The pair of hollows 113$a$ are preferably provided at, but not limited to, both ends of the cartridge. For example, the pair of hollows 113$a$ may be provided at a certain distance from each other in the longitudinal direction of the cartridge 113. The information storage medium 113$b$ may be a QR code (registered trademark), a barcode, an IC tag or the like. The integrated cartridge 113 further comprises one recessed groove (pin insertion part) 113$f$ near the center crossing the longitudinal direction of the cartridge. As shown in FIGS. 17 and 18, the cartridge securing mechanism comprises a pin 113$g$ that can be inserted and removed from the recessed groove 113*f* from the side of the cartridge 113, a pin support 113*h* for movably supporting the pin 113*g*, and a moving mechanism (not shown) such as an actuator for moving the pin support 113*h*.

The operation of the cartridge securing mechanism will be described. In FIGS. 17 and 18(*c*), the pin 113*g* is inserted into the recessed groove 113*f*. As shown in FIG. 18(*a*), the cartridge such as the integrated cartridge 113 is lowered from above by a cartridge picker 2540 (FIG. 31) towards the treatment lane 2310 of the stage racks 2300 and loaded in the treatment lane 2310 at a certain position. Thereafter, as shown in FIGS. 17 and 18(*c*), the pin 113*g* is inserted into the recessed groove 113*f* to secure the cartridge 113. The cartridge 113 is secured so as to prevent the cartridge 113 from floating or falling upon transfer and installation of the stage racks 2300. The pin 113*g* and the pin support 113*h* are provided below the stage racks 2300, where the pin support 113*h* is slid by a sliding mechanism provided on the stage racks 2300 or the like. Although a recessed groove provided in the integrated cartridge 113 has been described, the integrated cartridge 113 may not be used and recessed grooves may be provided in an extraction cartridge and a PCR cartridge instead, so as to secure the recessed grooves with pins.

[Cartridge Supply Module]

Figure 19:
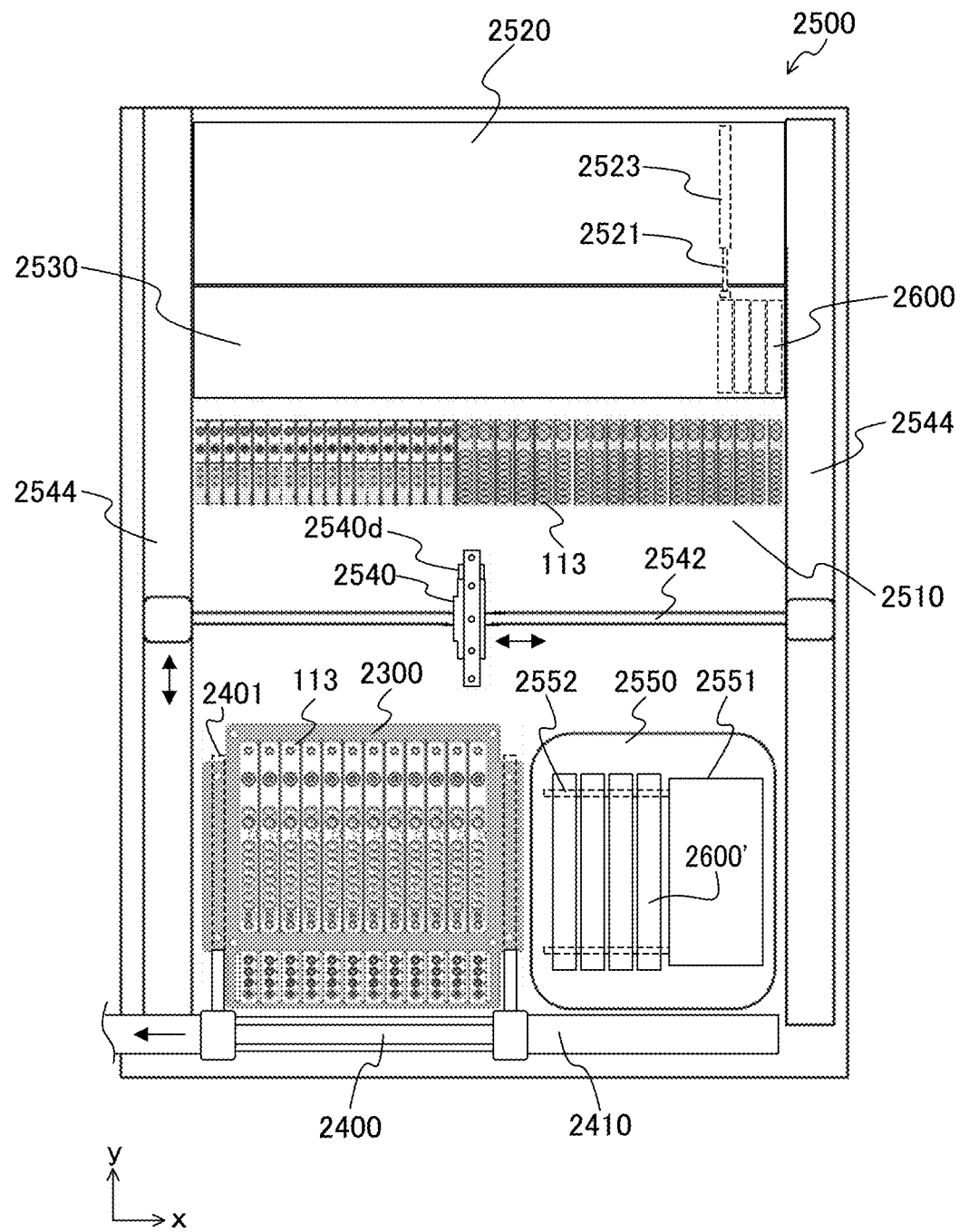
FIG. 19 A top view of a cartridge supply module provided in the first embodiment of the present invention.

As can be appreciated from FIG. 19, the cartridge supply module 2500 comprises the cartridge supply stage 2510, an accommodating shelf 2530 provided behind the cartridge supply stage 2510 for accommodating the cartridge, a cartridge push-out section 2520 provided behind the accommodating shelf 2530, a cartridge picker 2540 which is three-dimensionally movable above the cartridge supply stage 2510, and a cartridge discard box 2550 provided in front of the cartridge supply stage 2510. The cartridge picker 2540 comprises a x-direction transferring motor 2540*c* for moving in the x-direction along the first rail 2542 shown in FIG. 19 (FIG. 31), and a y-direction transferring motor (not shown) for moving in the y-direction along the second rails 2544. The cartridge discard box 2550 is disposed obliquely below the stage racks 2300 that has moved to the cartridge supply module 2500. The used cartridges are discarded in the cartridge discard box 2550 using the cartridge picker 2540.

The structure of the cartridge picker 2540 provided in the cartridge supply module 2500 will be described with reference to FIG. 31. The cartridge picker 2540 comprises a plurality of suction parts (projections) 2540*a* for suctioning the plurality of hollows 113*a* of the cartridge 113, an elevating motor 2540*b* for raising/lowering the plurality of suction parts 2540*a* in the z-direction, and a transferring motor 2540*c* for moving the cartridge picker 2540 in the x-direction along the first rail 2542. Each of the plurality of suction parts 2540*a* has a conically protruding shape with a suction port at the tip, where the suction port is connected with a vacuum pump (not shown). The cartridge 113 is picked up by moving the cartridge picker 2540 above the cartridge 113 and lowering the pair of suction parts 2540*a* as represented by the dashed line to suction the cartridge 113. The cartridge picker 2540 is raised while suctioning the cartridge 113, and moved to the treatment lane 2310 of the stage racks 2300 to mount the cartridge in the treatment lane 2310.

The pair of suction parts 2540*a* are supported by a suction part support member 2540*e*. Preferably, the suction part support member 2540*e* is provided with a ranging mechanism so as to alter the distance between the pair of suction parts 2540 according to the cartridges having different longitudinal dimensions to allow these cartridges to be picked up. When a ranging mechanism is not provided, a plurality of suction part support members having different lengths can be provided to allow cartridges with different dimensions to be picked up. Furthermore, the cartridge picker 2540 comprises a carton information readout unit 2540*d* and/or a cartridge information readout unit 2540*f* for reading out information from a carton information storage medium 2601*b* (FIG. 20) and/or a cartridge information storage medium 113*b* (FIG. 16), respectively.

[Cartridge Carton]

Figure 22:
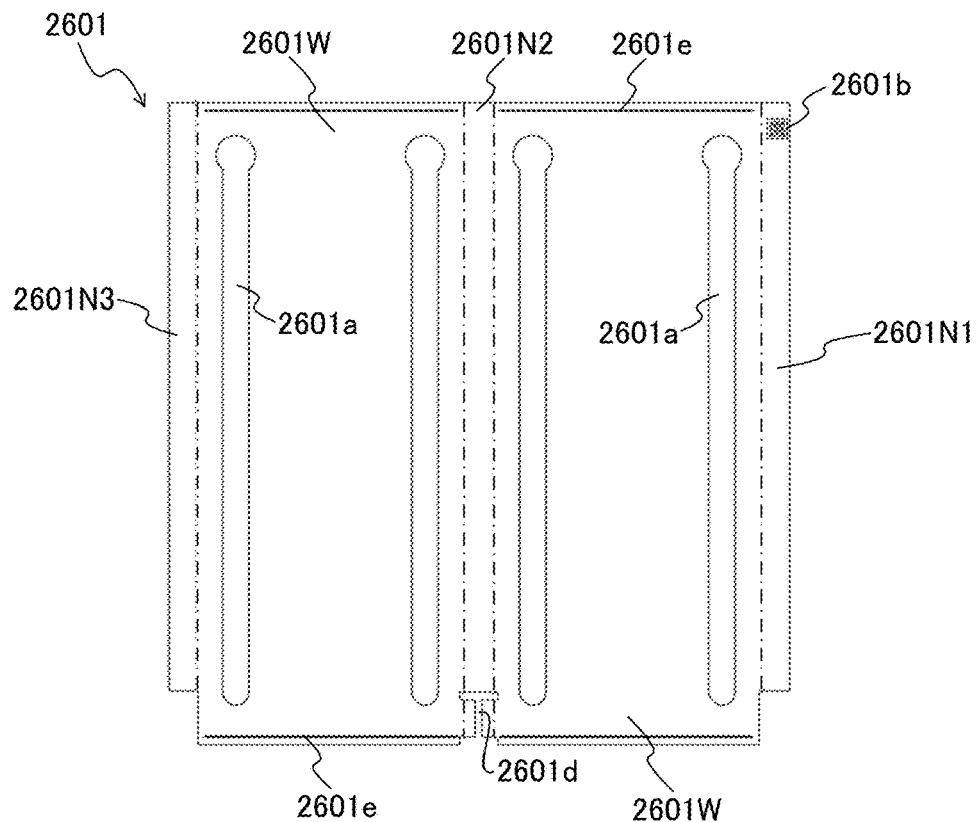
FIG. 22 An expanded view of a plate material forming the side surfaces of the cartridge carton shown in FIG. 20.
Figure 23:
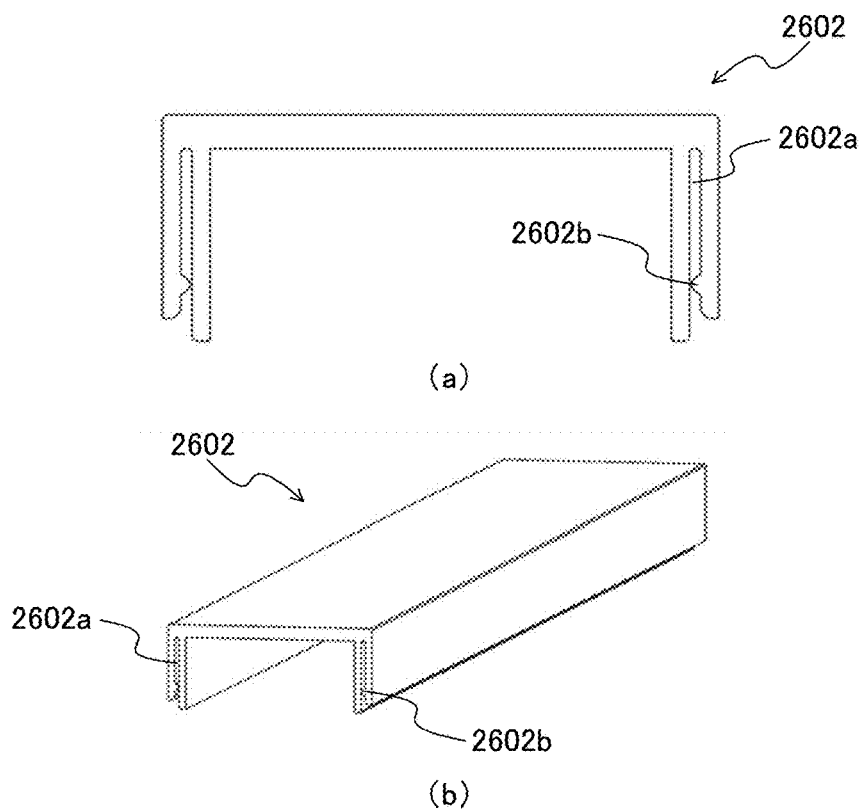
FIG. 23(a) A front view and (b) a perspective view of a cap member forming the upper surface and the bottom surface of the cartridge carton shown in FIG. 20.

A structure of a cartridge carton (book-type carton) 2600 which is accommodated in the accommodating shelf 2530 will be described with reference to FIGS. 20-23. As can be appreciated from FIG. 22, the cartridge carton 2600 is a flat container that accommodates cartridges such as the integrated cartridges 113 in a stack. The cartridge carton 2600 is composed of a plate-like side surface member 2601 whose expanded view is shown in FIG. 22, and cap members 2602 forming the upper and bottom surfaces as shown in FIG. 23. The cartridge carton 2600 is preferably formed of a transparent or translucent resin material, and is capable of accommodating twelve cartridges in a stack. As can be appreciated from FIG. 20, at least one slot (slim opening) 2601*a* is formed in each of the pair of wider surfaces 2601W of the side surface member 2601. The upper part of the first narrower surface 2601N1 is provided with the carton information storage medium 2601*b* such as a QR code (registered trademark), a barcode, an IC tag or the like. The carton information storage medium 2601*b* stores the type, production number, shelf life and/or the like of the cartridges accommodated in the cartridge carton 2600, which can be read out by the cartridge information readout unit 2540*d* (FIGS. 19 and 31). The carton information storage medium 2601*b* may be a QR code (registered trademark), a barcode, an IC tag or the like.

Figure 20:
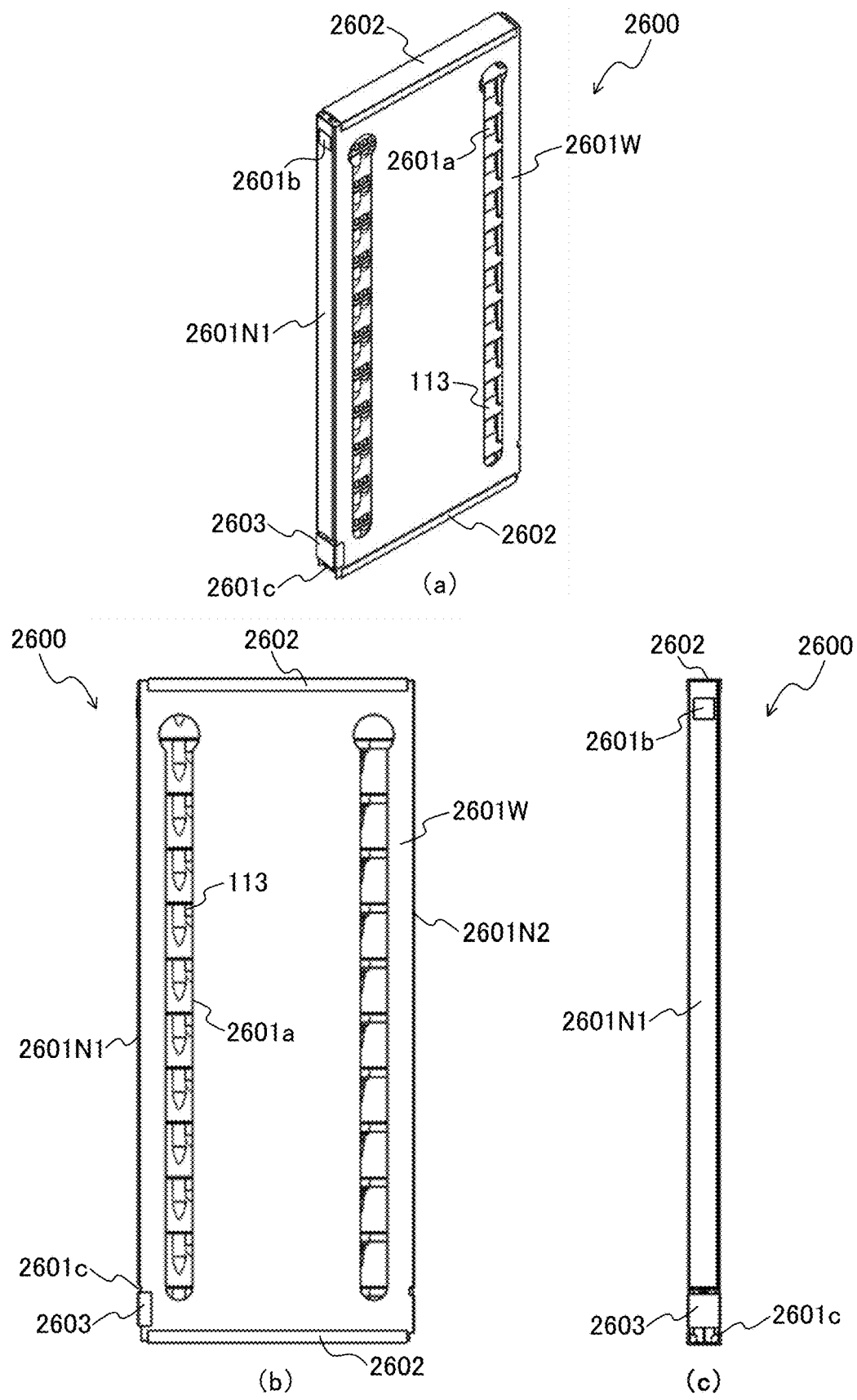
FIG. 20(a) A perspective view of a cartridge carton provided in the cartridge supply module shown in FIG. 19, (b) a side view of the cartridge carton on the wider surface side, and (c) a side view of the cartridge carton on the narrower surface side.
Figure 21:
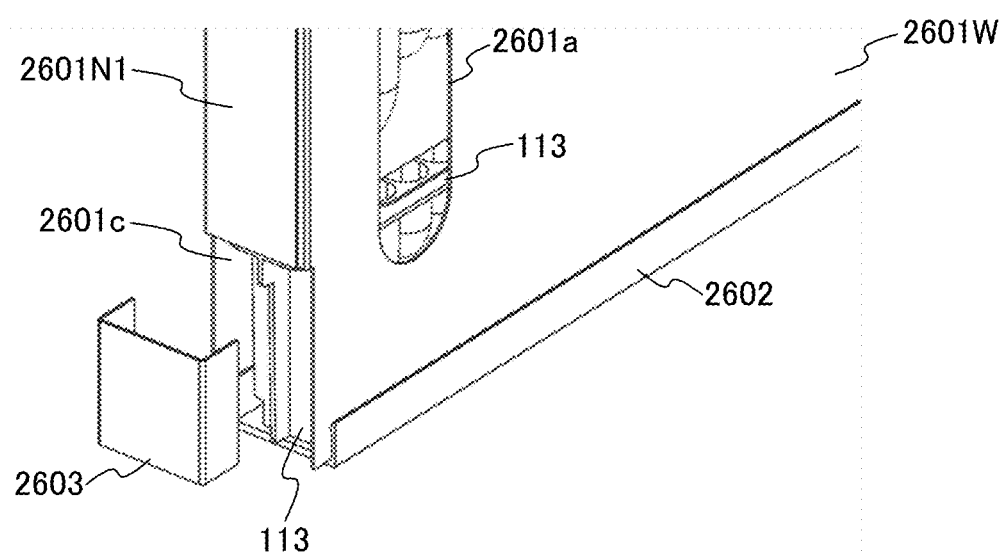
FIG. 21 A perspective view of a lower part of the cartridge carton shown in FIG. 20.

As can be appreciated from FIGS. 20 and 21, a push-out opening 2601*c* for pushing out the cartridges is formed in the lower part of the first narrower surface 2601N1, where the push-out opening 2601*c* is covered with a seal plate 2603. The seal plate 2603 is removed before pushing out the cartridges. As shown in FIG. 22, a bar insertion opening 2601*d* for inserting a push-out bar 2521 (FIG. 25) for pushing the cartridges is formed in the lower part of the second narrower surface 2601N2 of the side surface member 2601. Slim hollows or openings 2601*e* are formed in the upper and lower ends of the wider surfaces 2601W.

Figure 24:
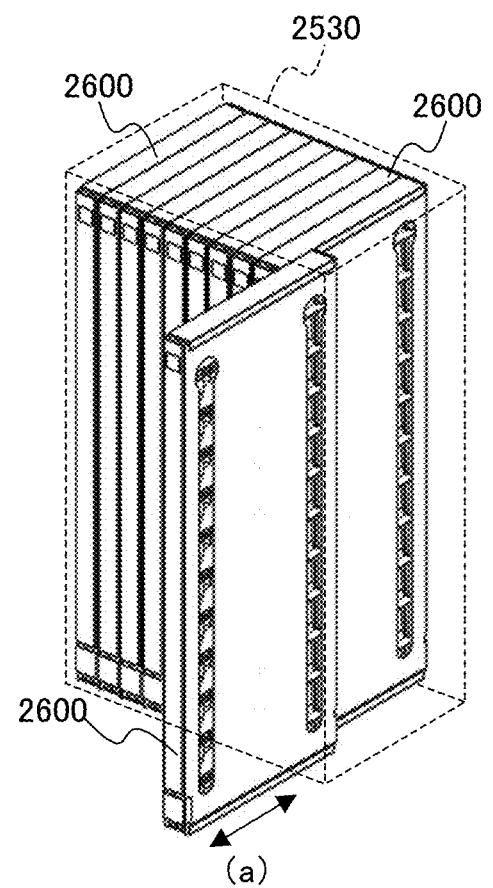
FIG. 24 A perspective view of the cartridge cartons shown in FIG. 20 which are arranged side by side in an accommodating shelf.
Figure 24:
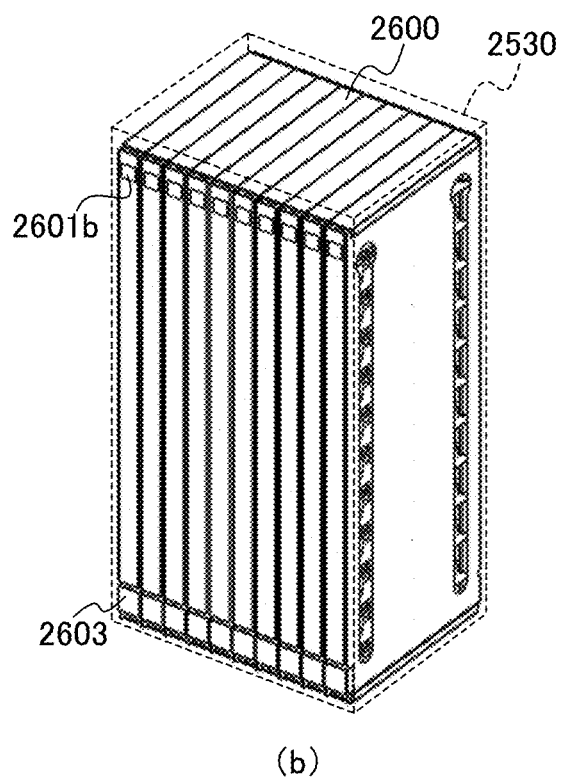

The side surface member 2601 shown in FIG. 22 is folded along the dash-dotted line, where a third narrower surface 2601N3 is adhered to the first narrower surface 2601N1 so as to form a rectangular prism. The cap members 2602 are attached to the top and the bottom of the side surface member 2601 having the rectangular prism shape so as to form a box. As can be appreciated from FIG. 23, each of the pair of walls of the cap members 2602 is provided with a slit 2602*a*, inside which a projection 2602*b* is formed. When the cap members 2602 are attached to the side surface member 2601 having the rectangular prism shape, the projection 2602*b* fits the slim hollow 2601*e*, by which the cap members 2602 are secured to the side surface member 2601. The plurality of cartridge cartons 2600 are accommodated in the accommodating shelf 2530 as shown in FIG. 24. Here, the cartridge cartons 2600 are secured to the accommodating shelf 2530 by a securing mechanism (not shown) while being accommodated in the accommodating shelf 2530.

Next, the push-out mechanism 2520 for pushing out a cartridge such as the integrated cartridge 113 from the cartridge carton 2600 onto the cartridge supply stage 2510 will be described. As shown in FIG. 19, the push-out mechanism 2520 is composed of a push-out bar 2521, an actuator 2523 for stretching the push-out bar 2521 in the y-direction, and an elevating mechanism (not shown) for the push-out bar 2521 and the actuator 2523. While FIG. 19 shows only one set of push-out bar 2521 and actuator 2523, a plurality of push-out bars 2521 and actuators 2523 are provided in correspondence with the plurality of cartridge cartons 2600.

Figure 25:
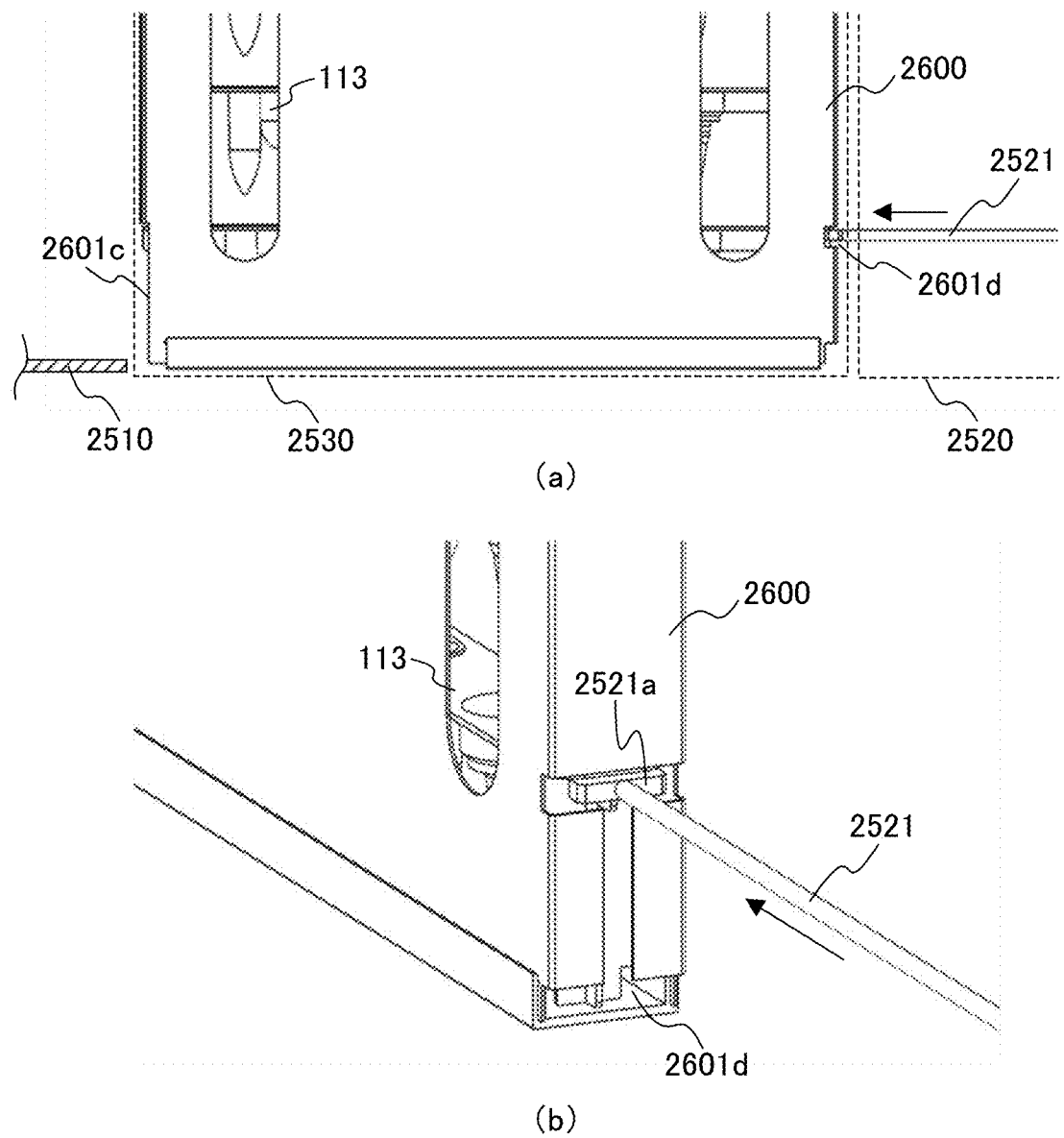
FIG. 25(a) A side view and (b) a perspective rear view of a state before the cartridge is pushed out from the cartridge carton.

Next, an operation of the push-out bar 2521 for pushing out the cartridge 113 from the cartridge carton 2600 will be described with reference to FIGS. 25-28. As shown in FIG. 25(b), the push-out bar 2521 has a T-shaped pushing out end part 2521a. In FIG. 25, the pushing out end part 2521a is placed inside the cartridge carton 2600 in the vicinity of the upper wide part of the bar insertion opening 2601d of the cartridge carton 2600. In this state, the pushing out end part 2521a abuts the rear end of the integrated cartridge 113 accommodated in the cartridge carton 2600. As the push-out bar 2521 shown in FIG. 25 is moved in the direction represented by the arrow, it reaches the state shown in FIG. 26.

Figure 26:
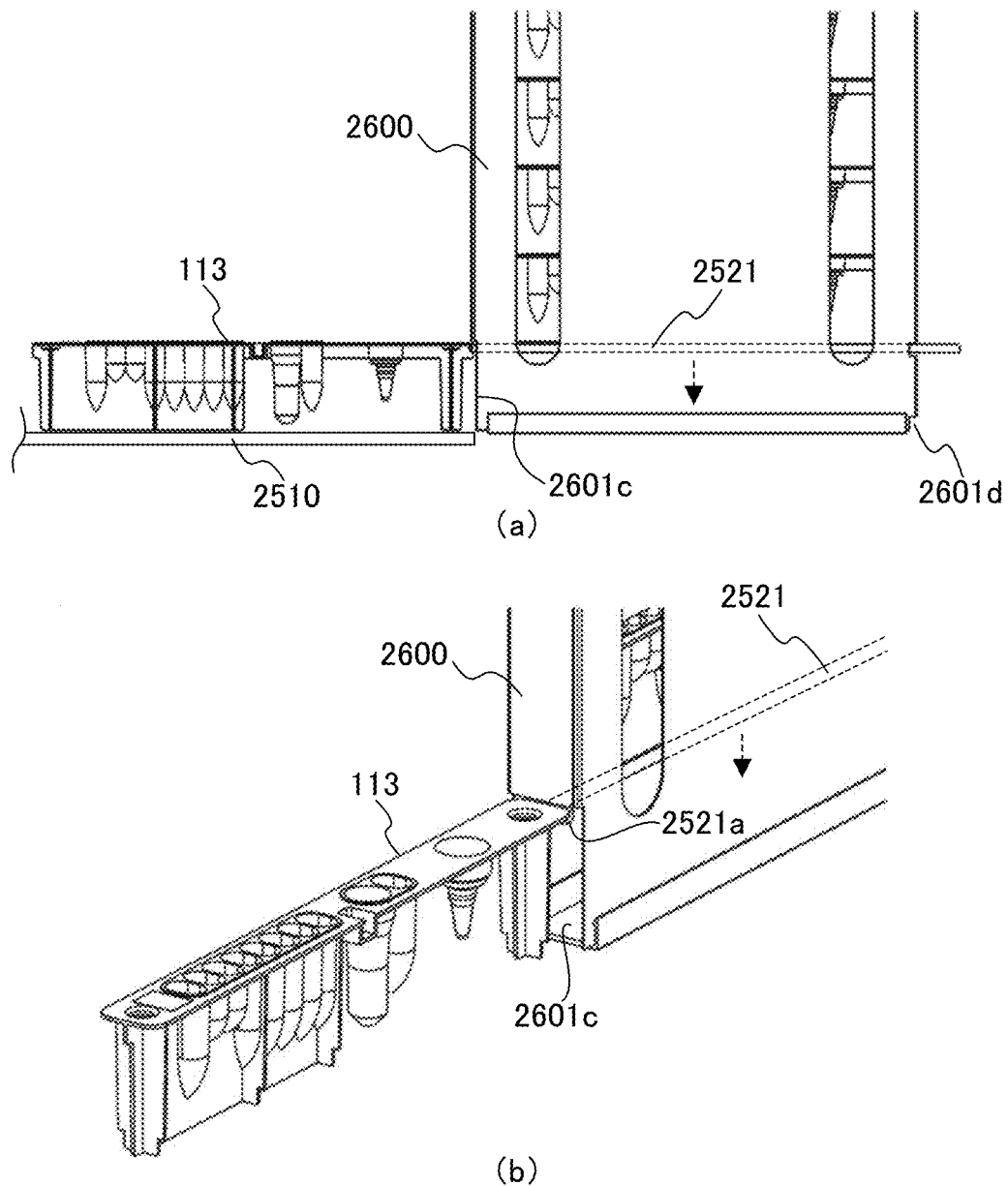
FIG. 26(a) A side view and (b) a perspective front view of a state after the cartridge has been pushed out from the cartridge carton.
Figure 27:
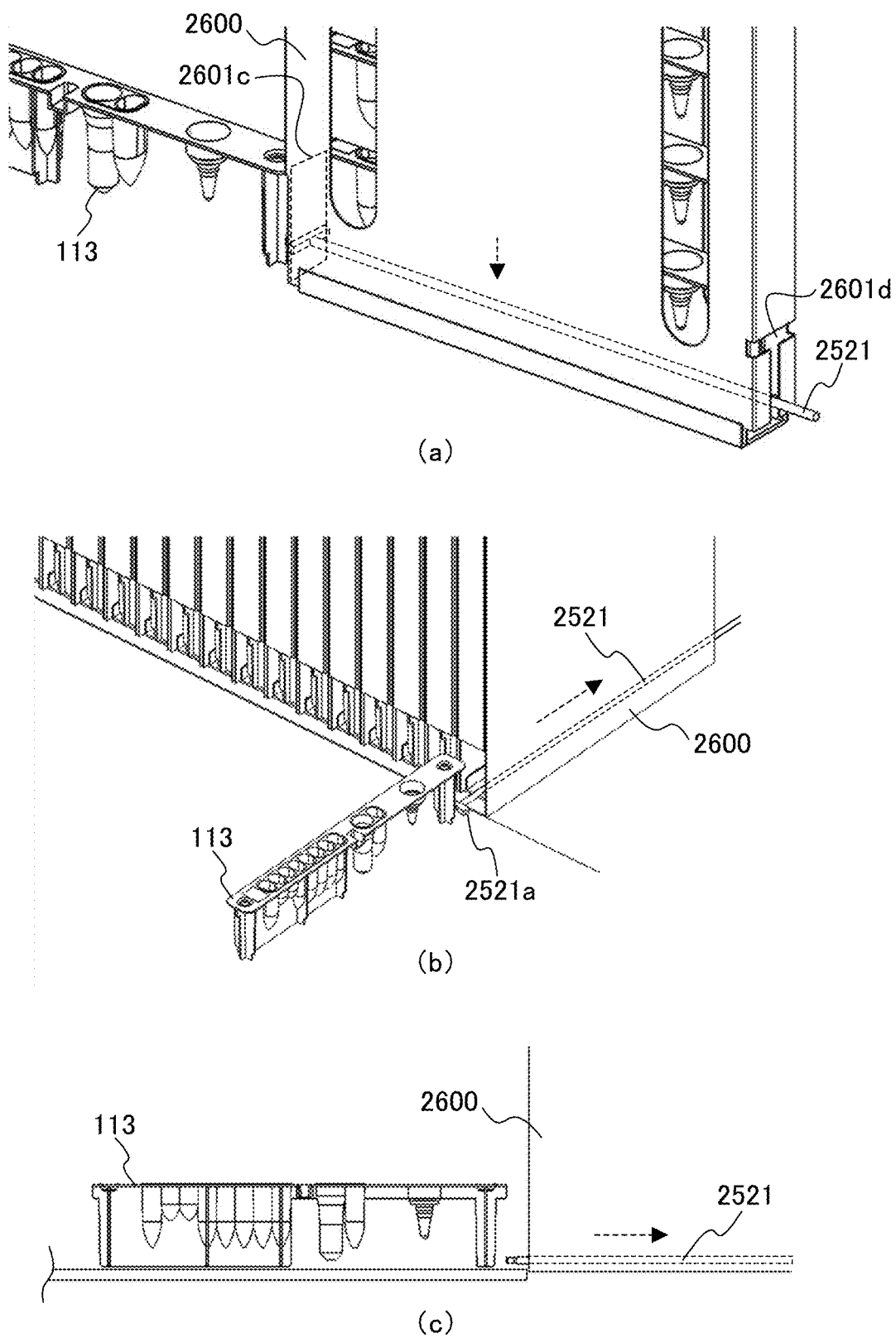
FIG. 27(a) A perspective rear view (b) a perspective front view and (c) a side view of a state where the push-out bar has been lowered from the state shown in FIG. 26.

In FIG. 26, the push-out bar 2521 moves inside the cartridge carton 2600 until the pushing out end part 2521a reaches the push-out opening 2601c, whereby the cartridge 113 in the bottommost row is completely pushed out on the cartridge supply stage 2510. As the push-out bar 2521 shown in FIG. 26 is lowered in the direction indicated by the arrow by the elevating mechanism, it reaches the state shown in FIG. 27(a). As the push-out bar 2521 is gradually lowered, the plurality of cartridges 113 stacked on the push-out bar 2521 are gradually lowered as well. Thus, for example, breakage due to sudden fall of the plurality of cartridges 113 can be prevented.

Figure 28:
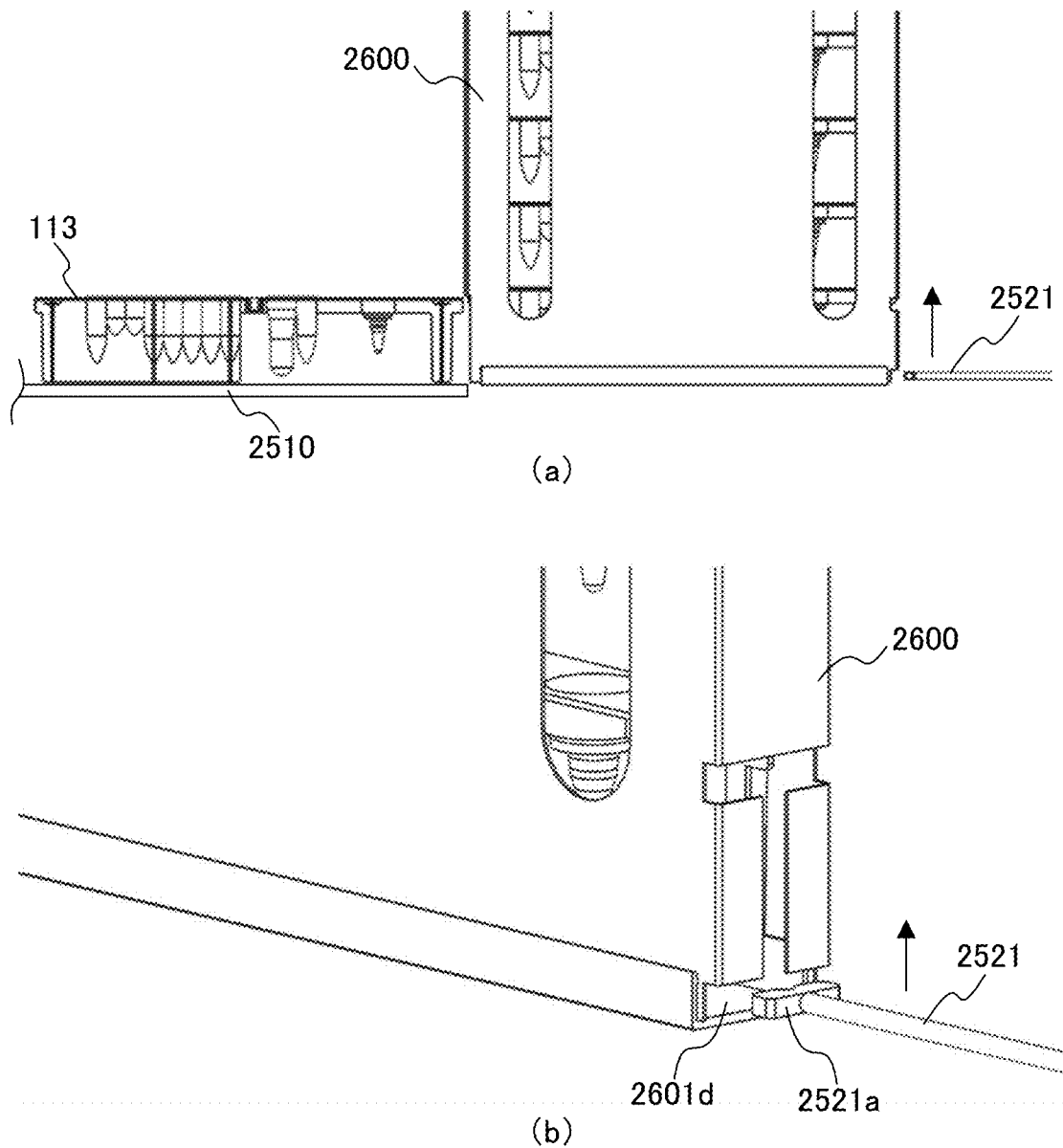
FIG. 28(a) A side view and (b) a perspective rear view of a state where the push-out bar has been retreated from the state shown in FIG. 27.

As the push-out bar 2521 is lowered near the bottom surface of the cartridge carton 2600 as shown in FIG. 27(b), the push-out bar 2521 is pulled out from the cartridge carton 2600 as shown in FIG. 27(c). In FIG. 28, the push-out bar 2521 is completely taken out from the cartridge carton 2600. The pushing out end part 2521a is taken out from the lower wide part of the bar insertion opening 2601d of the cartridge carton 2600. For the next operation of pushing out the cartridge, the push-out bar 2521 shown in FIG. 28 is raised by the elevating mechanism to reach the state shown in FIG. 25.

Figure 29:
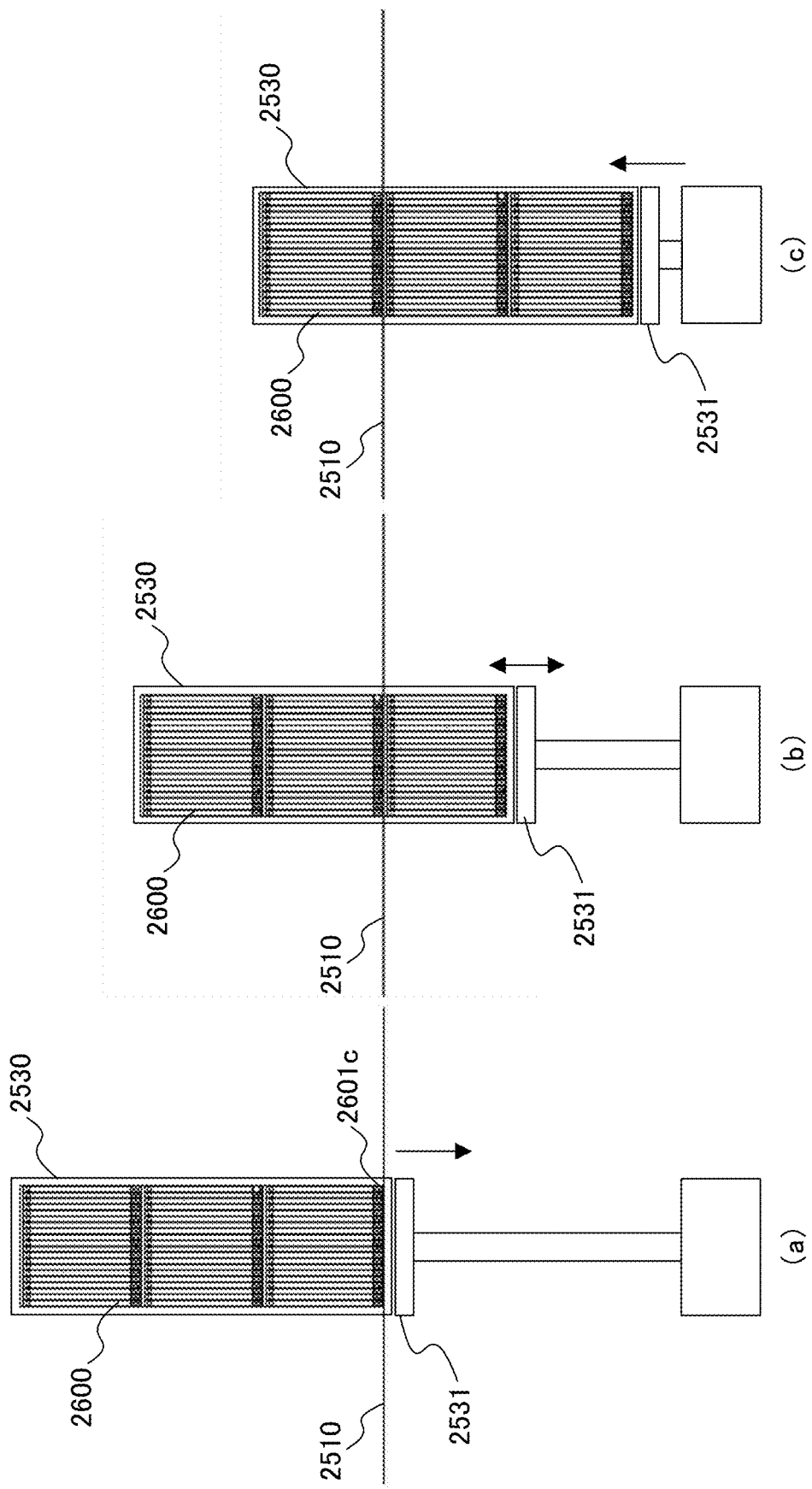
FIG. 29 Front views showing the states where the accommodating shelf accommodating the cartridge cartons is raised/lowered.

In FIG. 29, the accommodating shelf 2530 is shown as is a plurality of stacked shelves which can be raised/lowered. Each of the shelves accommodates a plurality of cartridge cartons 2600. The accommodating shelf 2530 is raised/lowered by a shelf elevating mechanism 2531 so that the shelves are brought to the same height as the cartridge supply stage 2510. The plurality of shelves may be, for example, three, and different types of cartridges may be stored in the respective shelves.

[Operation of Specimen Treatment and Measurement System]

In order to realize an efficient and high-throughput pretreatment step, the specimen treatment and measurement system 2000 according to the first embodiment operates as follows. First, a preparation operation in the cartridge supply module 2500 will be described. As shown in FIG. 19, the stage rack 2300 is moved to the cartridge loading position in the cartridge supply module 2500. The cartridge push-out mechanism 2520 pushes out the cartridge 113 onto the cartridge supply stage 2510. The cartridge 113 supplied onto the cartridge supply stage 2510 is loaded on the stage rack 2300 by the cartridge picker 2540. The cartridge 113 loaded on the stage rack 2300 is secured to the stage rack 2300 by the securing mechanism (FIGS. 17 and 18), thereby completing loading of the cartridge 113. Once the loading of the cartridge 113 is completed, the stage rack 2300 is transferred to the consumable supply module 2100 by the stage rack transferring mechanism 2400.

Next, a preparation operation in the consumable supply module 2100 will be described. As shown in FIG. 6, the stage rack 2300 is moved to the consumable loading position in the consumable supply module 2100. Consumables such as the dispenser chips, piercing chips and the like stored in the consumable storage section 2140 are picked up four at a time by a quadruple consumable picker 330 of the pick-up unit 300 (FIGS. 7 and 8) and loaded into the stage rack 2300. Consumables such as reagent containers and/or secondary specimen containers stored in the container storage section 2150 are also picked up four at a time by the quadruple consumable picker 330 of the pick-up unit 2130 and loaded on the stage rack 2300.

The various reagents such as a PCR reagent stored in the reagent storage section 2152 are dispensed into the reagent containers loaded on the stage rack 2300 by the dispenser nozzles 320 of the pick-up unit 300 (FIGS. 7 and 8). The primary specimen stored in the primary specimen tray 2160b of the primary specimen storage section 2160 is dispensed into the secondary specimen containers 2320 loaded on the stage rack 2300 by the dispenser nozzles 320 of the pick-up unit 300. Once the various consumables and else are placed on the stage rack 2300, the stage rage 2300 is transferred to the treatment execution module 2200 by the stage rack transferring mechanism 2400.

As shown in FIG. 9, the stage rack 2300 transferred to the treatment execution module 2200 is installed into the stage rack installation section 2210 by the stage rack installing mechanism 2250 (FIGS. 11-15). The stage rack 2300 is lowered by the elevating mechanism while being installed in the stage rack installation section 2210 so that the PCR well provided in the cartridge 113 on the stage rack 2300 makes close contact with a heat block (a heating/cooling unit such as a Peltier device) provided in the stage rack installation section 2210, thereby completing the installation operation. Once the operation of installing the stage rack 2300 is completed, the treatment execution unit 400 moves above the stage rack 2300 to execute each of the treatments, namely, DNA extraction and purification from the specimen, amplification and a measurement by real-time PCR or the like.

Once the above-mentioned treatments by the treatment execution unit 400 is completed, the dispenser nozzles of the treatment execution unit 400 are used to discharge the waste liquid on the stage rack 2300 into the waste liquid tank 2232, and then the consumables on the stage rack 2300 are discarded in the consumable discard box 2230. After the consumables are discarded and the waste liquid is discharged, the stage rack installing mechanism 2250 detaches the stage rack 2300 from the stage rack installation section 2210 and loads the stage rack 2300 in the stage rack moving mechanism 2400. This stage rack 2300 is transferred to the cartridge supply module 2500, where the cartridge 113 is discarded in the cartridge discard box 2550 by the cartridge picker 2540.

[Discarded Cartridge Aligning Unit]

As can be appreciated from FIG. 19, a plurality of cartridge cartons 2600' are arranged in the cartridge discard box 2550 for accommodating the discarded cartridges in a stack. The cartridge carton 2600' refers to one with an open upper surface that can be obtained by removing the cap member 2602 from the upper surface of the empty cartridge carton 2600. A discarded cartridge aligning unit 2551 is provided in the cartridge discard box 2550. The discarded cartridge aligning unit 2551 comprises a pair of elevating arms 2552, and an elevating mechanism for the elevating arms 2552. The pair of elevating arms 2552 are inserted into a pair of slots 2601a of the cartridge carton 2600'. In this state, the discarded cartridge aligning unit 2551 positions the pair of elevating arms 2552 near the upper surface opening of the cartridge carton 2600' so as to allow the first discarded cartridge to be mounted on the elevating arms 2552 by the cartridge picker 2540. Subsequently, the discarded cartridge aligning unit 2551 lowers the elevating arms 2552 for the height of the discarded cartridge so that the second discarded cartridge can be mounted on the first discarded cartridge. By repeating this, the discarded cartridges can be aligned and stacked in the cartridge carton 2600'. Thus, cartridges can automatically be aligned upon discarding the cartridges, which allows reduction in the volume of discards as compared to the case where the cartridges are disorderly accommodated to be discarded.

[Modification of Module Arrangement]

Figure 30:
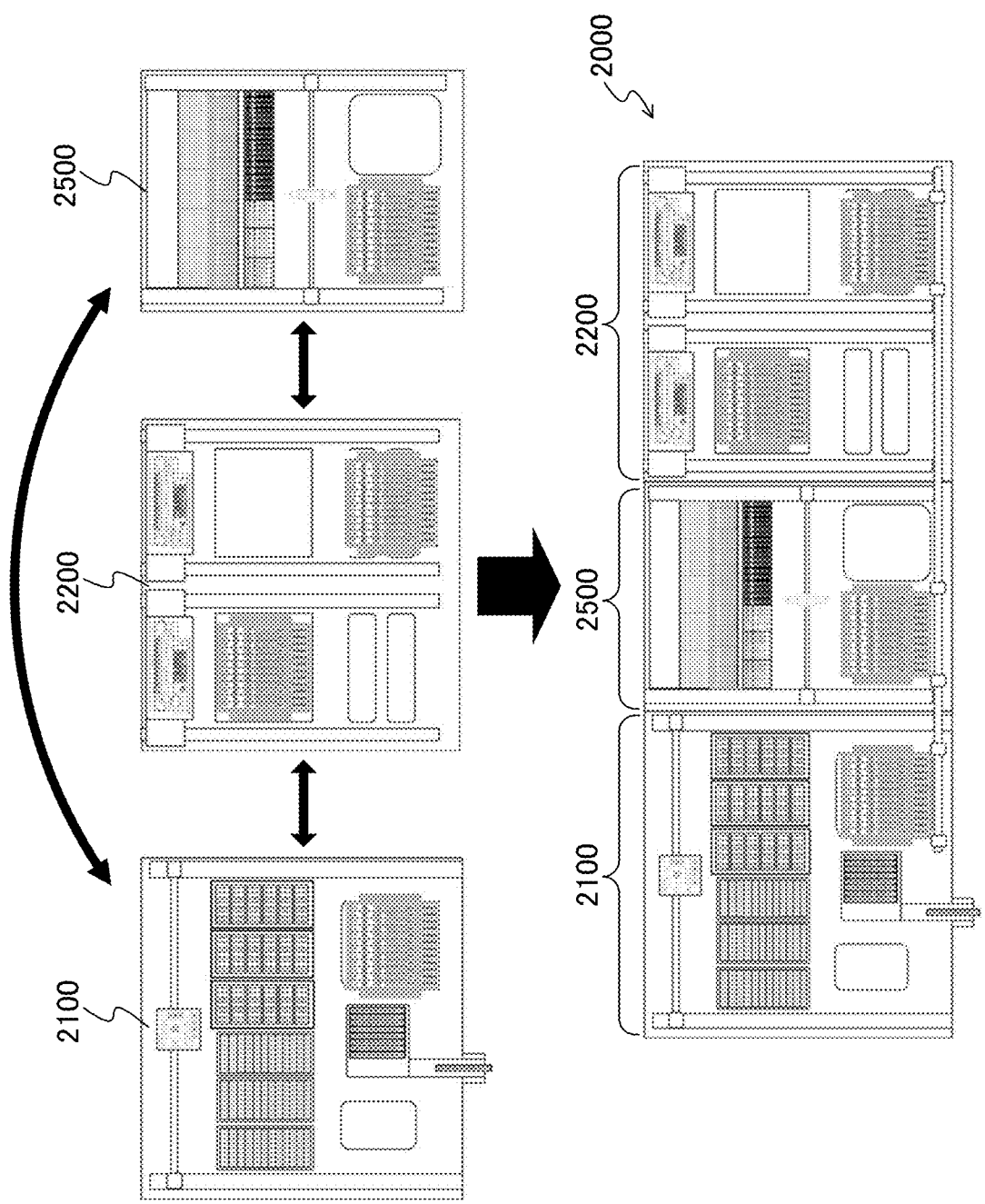
FIG. 30 A schematic view showing a modified example of the module arrangement of the specimen treatment and measurement system shown in FIG. 4.

In the specimen treatment and measurement system 2000, the arrangement of each module can freely be modified. Although the consumable supply module 2100, the treatment execution module 2200 and the cartridge supply module 2500 are arranged in this order from the left in FIG. 4, the present invention is not limited thereto. For example, the consumable supply module 2100, the cartridge supply module 2500 and the treatment execution module 2200 may be arranged in this order from the left as shown in FIG. 30.

[Fractionating and Storing Extract]

The specimen extract storage section 2170 shown in FIG. 6 is capable of fractionating and storing a part of the extract such as DNA which has been extracted by the treatment execution units 400 in the treatment execution module 2200. In order to fractionate and store a part of the extract, the operation of the treatment execution unit 400 is paused after the DNA extraction/purification steps, and the stage rack 2300 is transferred from the treatment execution module 2200 to the consumable supply module 2100. Once the stage rack 2300 is transferred to the consumable supply module 2100, a part of the extract is moved from the extract wells of the cartridges 113 on the stage rack 2300 to one or a plurality of extract storing tubes 2170a of the specimen extract storage section 2170 by using the dispenser nozzles 320 of the pick-up unit 300 (FIGS. 7 and 8). The extract storing tubes 2170a for storing a part of the extract are sealed with caps or the like, and cooled and stored preferably at about 4° C. by the cooling mechanism of the specimen extract storage section 2170. After storing a part of the extract, the stage rack 2300 is transferred from the consumable supply module 2100 to the treatment execution module 2200 so as to execute amplification, a measurement and the like for the DNA in the extract by the treatment execution unit 400. The part of the extract stored in the extract storing tubes 2170a can be used for other measurement (other gene test) that differs from the measurement conducted after restarting the treatment execution unit 400.

Next, a specific example relating to storage of a part of the extract will be described. For 50 ml of a DNA extract that has not yet been subjected to the PCR step, 10 ml of it may be subjected to PCR and a measurement, while the remaining 40 ml may be stored to be used for other test in the future. For example, when subject A is to be subjected to three tests for human immunodeficiency virus (HIV), hepatitis B virus (HBV) and hepatitis C virus (HCV), 10 ml is used upon extraction for conducting only high priority HIV testing. Later, the partially stored DNA extract (40 ml) can be used to execute any of the tests. Accordingly, the DNA extract is not wasted.

[Dividing Extract]

The extract such as DNA extracted by using the treatment execution unit 400 in the treatment execution module 2200 may be divided into other treatment lanes to execute the treatment and the measurement. When the extract is to be divided, the operation of the treatment execution units 400 is paused after the DNA extraction/purification steps, and the stage rack 2300 is transferred from the treatment execution module 2200 to the consumable supply module 2100. Once the stage rack 2300 is transferred to the consumable supply module 2100, the dispenser nozzles 320 are used to divide the extract in the extract well of the first cartridge 113 on the stage rack 2300 into an empty extract well of the second cartridge 113 on the stage rack 2300. After dividing the extract, the stage rack 2300 is transferred from the consumable supply module 2100 to the treatment execution module 2200, and the extracts divided into the first and second cartridges 113 are used to execute amplification, measurement and the like for the DNA in the extracts.

[Modified Embodiment of Cartridge Supply Module]

In the cartridge supply module 2500 shown in FIG. 19, the cartridge is pushed out from the cartridge carton 2600 onto the stage, and the pushed out cartridge is picked up by the cartridge picker 2540 to be mounted on the stage rack 2300. Alternatively, according to this modified embodiment, the cartridge is pushed from the cartridge carton 2600 directly into a stage rack 2700. According to this modified embodiment, the stage rack 2700 shown in FIGS. 32 and 33 is used instead of the stage rack 2300.

The structure of the stage rack 2700 according to this modified embodiment will be described with reference to FIGS. 32 and 33. The stage rack 2700 is substantially a plate, and comprises a substantially rectangular upper surface body 2701, a comb-shaped lower surface body 2703, and a plurality of openings 2707 penetrating through the upper surface body 2701 and the lower surface body 2703. The openings 2707 are defined by a plurality of rectangular openings formed in the upper surface body 2701 and the slits between the teeth of the lower surface body 2703. The lower surface body 2703 comprises a plurality of first rails 2703a which extend parallel to each other, and second rails 2703b which are provided along the sides of the stage rack 2700 and which extend parallel to the first rails 2703a. The first rails 2703a and the second rails 2703b make the teeth of the lower surface body 2703. The upper surface body 2701 and the lower surface body 2703 are preferably formed by cutting and/or punching out a metal plate. The formed upper surface body 2701 and the lower surface body 2703 are integrated by welding, caulking, screwing or the like.

Figure 32:
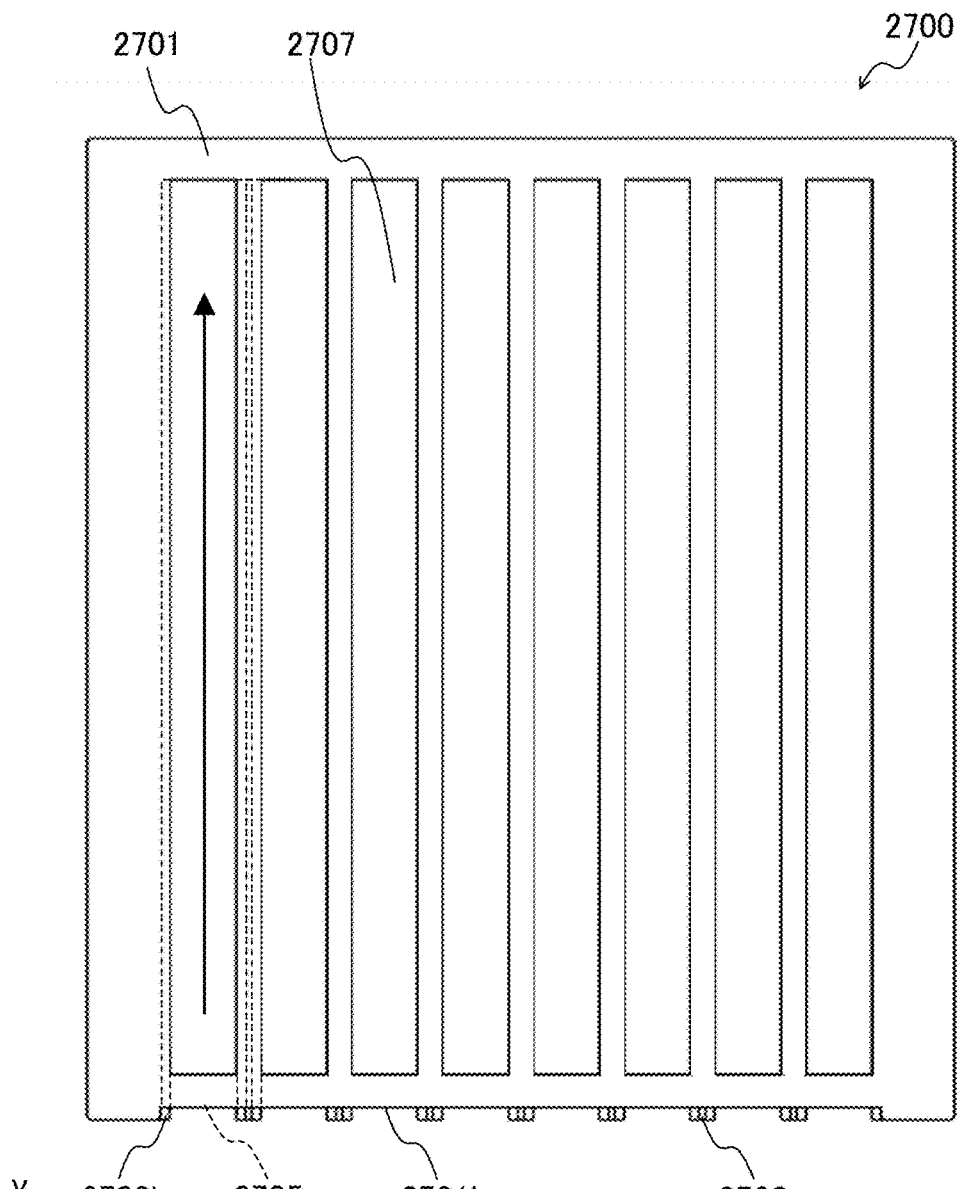
FIG. 32(a) A top view and (b) a side view showing a structure of a stage rack used for the modified embodiment of the present invention.
Figure 32:
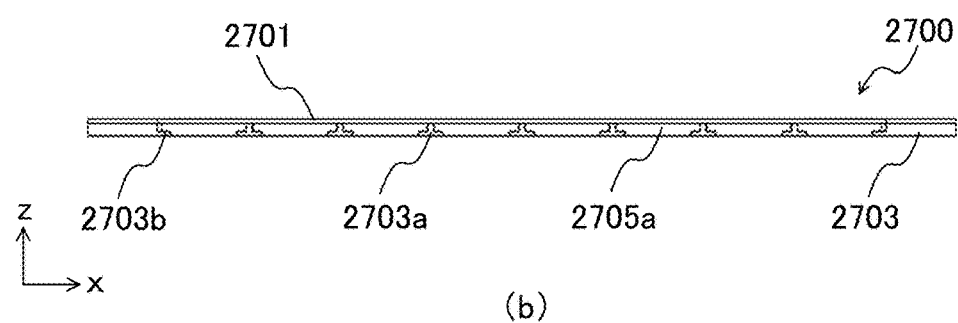
Figure 33:
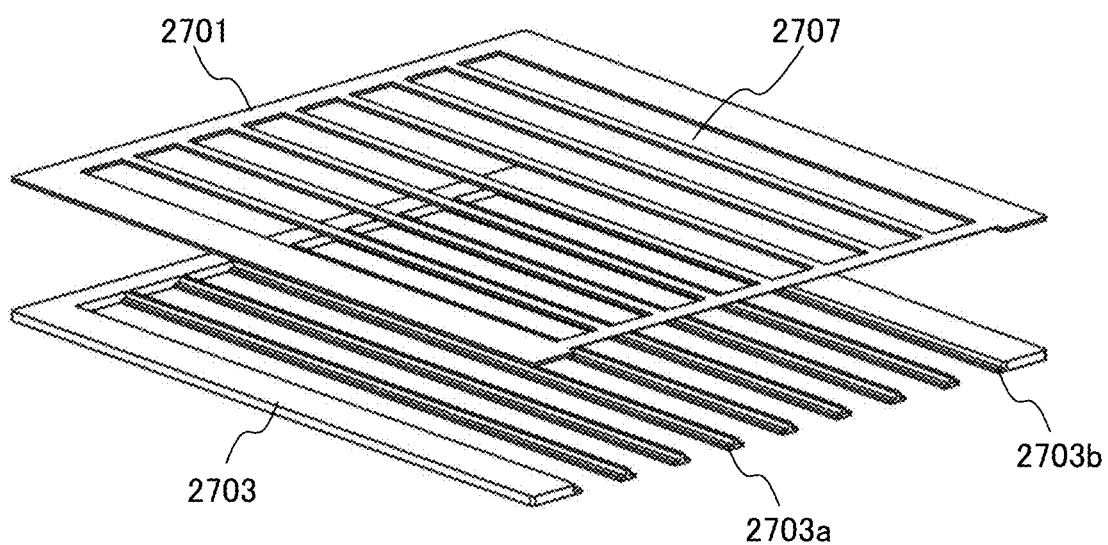
FIG. 33 An exploded perspective view of the stage rack shown in FIG. 32.

As can be appreciated from FIG. 32, a plurality of cartridge receiving ports 2705a are formed on a side of the stage rack 2700. As can be appreciated from FIG. 32(a), the ends of the first rails 2703a and the second rails 2703b are projecting out from the cartridge receiving ports 2705a. As shown in FIG. 32(b), the first rails 2703a have a vertically inverted T-shape when seen from the side while the second rails 2703b have an L-shape or a horizontally inverted L-shape when seen from the side. The openings 2707 between the respective rails define spaces for inserting cartridges. Each of the rails extends in the y-direction along the openings 2707. Along the arrow extending in the y-direction in FIG. 32(a), a later-described cartridge is pushed from the cartridge receiving port 2705a into the stage rack 2700.

Figure 34:
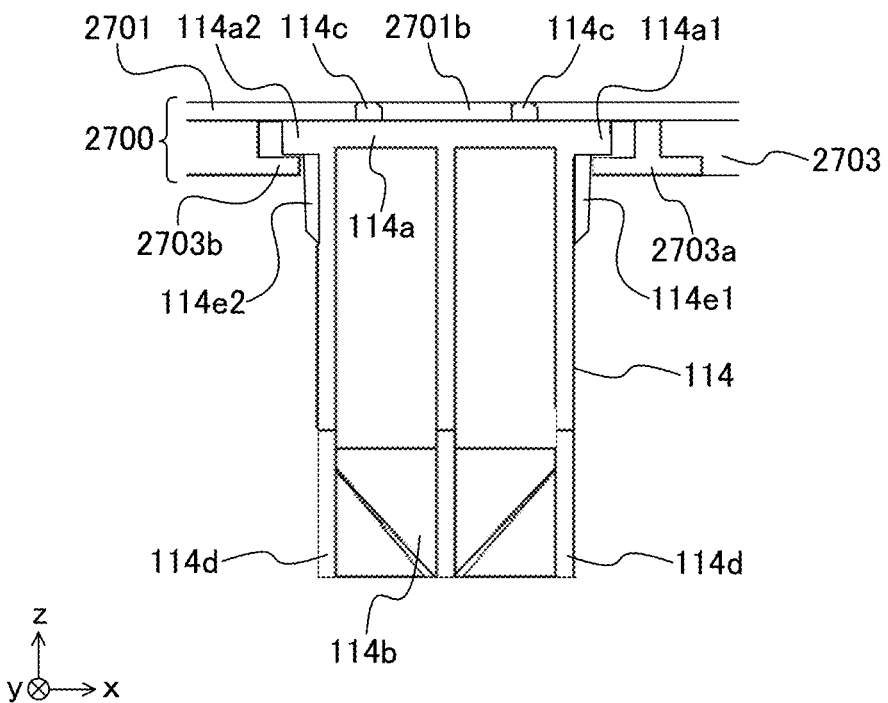
FIG. 34 A side view showing a state where a cartridge loaded on the stage rack shown in FIG. 32.

A state where a cartridge 114 is inserted into the stage rack 2700 will be described with reference to the side view shown in FIG. 34. One longitudinal edge 114a1 of the top surface plate 114a of the cartridge 114 is sandwiched between the upper surface body 2701 and the first rail 2703a. One side protrusion 114e1 of the cartridge 114 opposes the side surface of the first rail 2703a. The other longitudinal edge 114a2 of the top surface plate 114a of the cartridge 114 is sandwiched between the upper surface body 2701 and the second rail 2703b. The other side protrusion 114e2 of the cartridge 114 opposes the side surface of the second rail 2703b. Accordingly, while the movement of the cartridge 114 in the x- and z-directions is limited with respect to the stage rack 2700, it can slide in the y-direction along the rails. In FIG. 34, the cartridge 114 is slidably arranged using the upper surface body 2701, the first rail 2703a and the second rail 2703b. The arrangement, however, is not limited to the arrangement shown in FIG. 34, and the cartridge 114 may be slidably arranged using the upper surface body 2701 and the pair of adjacent first rails 2703a.

Figure 35:
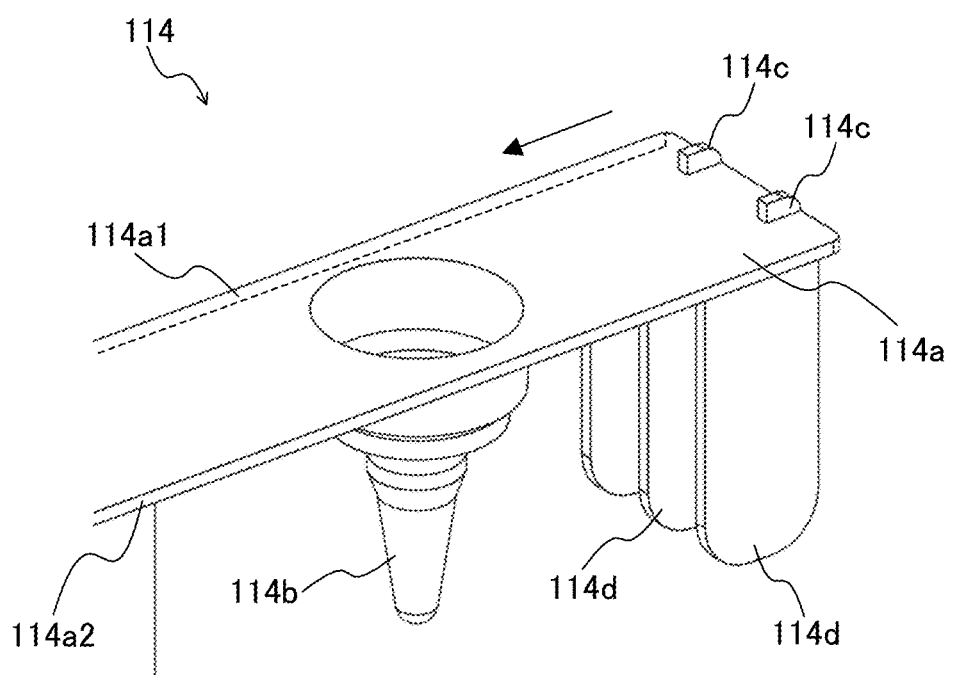
FIG. 35 A perspective view showing substantial parts of a cartridge used in the modified embodiment of the present invention.

The structure of the cartridge 114 will be described with reference to FIG. 35. The cartridge 114 comprises the top surface plate 114a, a well 114b that opens to the top surface plate 114a, at least one rib 114c that upwardly protrudes from the shorter side of the top surface plate 114a, and at least one rib 114d that downwardly protrudes from the shorter side of the top surface plate 114a. The top surface plate 114a comprises a pair of longitudinal edges 114a1 and 114a2 on its longer sides. When the cartridge 114 is pushed into the stage rack 2700, the cartridge 114 moves in the direction indicated by the arrow shown in FIG. 35. Upon this movement, the ribs 114d abut the outer side 2701b of the upper surface body 2701 (FIGS. 32 and 34) so as to limit the movement of the cartridge 114.

Figure 36:
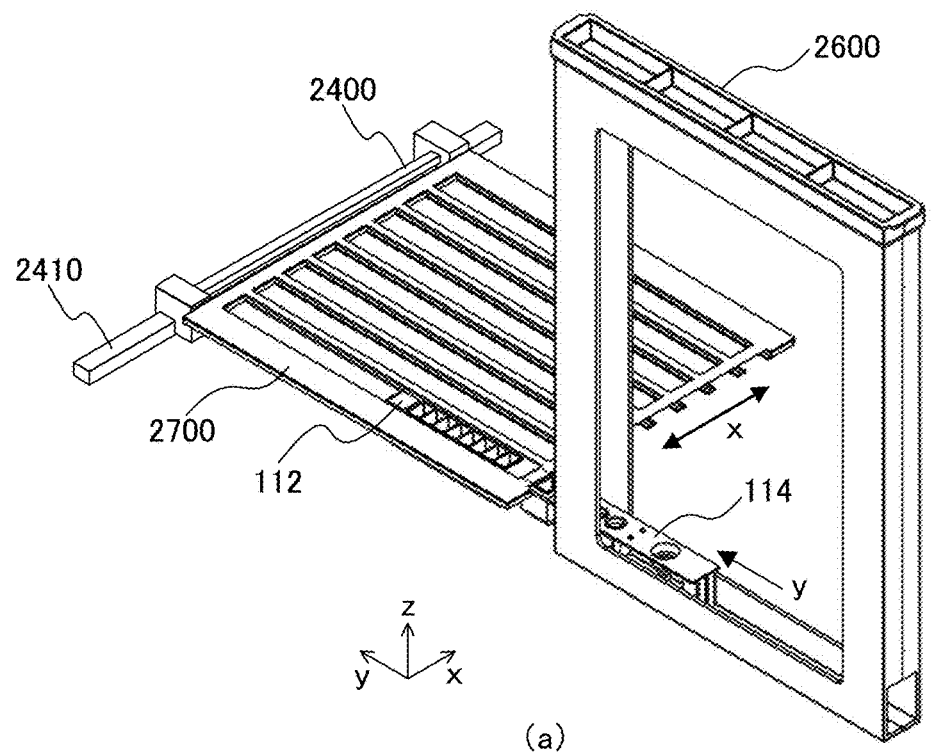
FIG. 36(a) A perspective rear view and (b) a perspective front view showing an arrangement of the cartridge carton with respect to the stage rack shown in FIG. 32.
Figure 36:
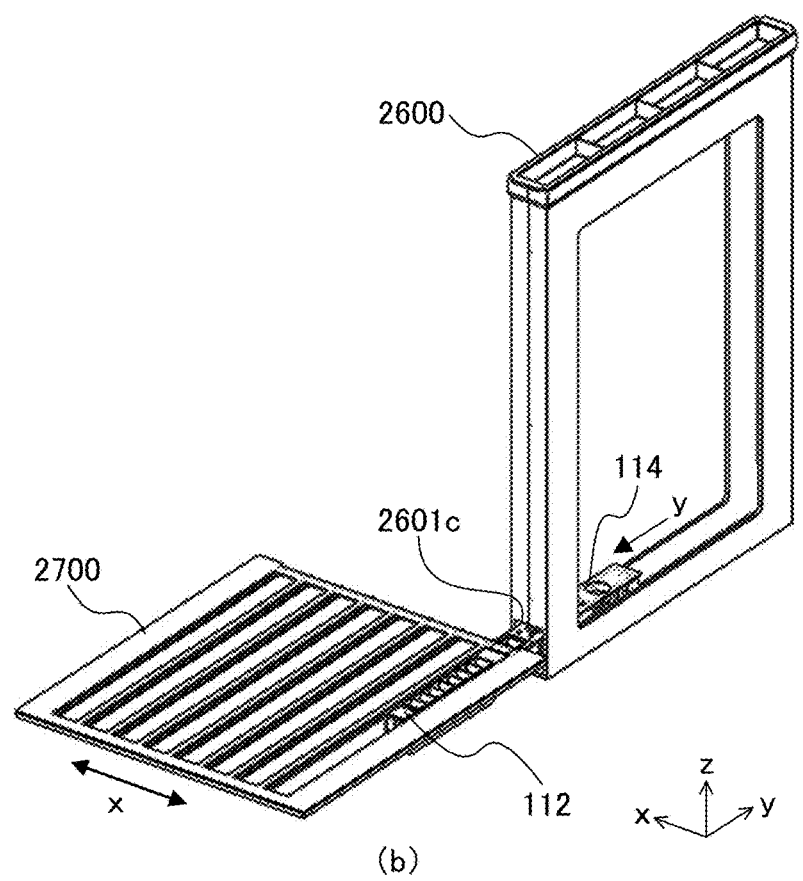

FIG. 36 shows relative positional relationship between the stage rack 2700 and the cartridge carton 2600. The stage rack 2700 and the cartridge carton 2600 are arranged in the cartridge supply module 2500. The cartridge push-out opening 2601c of the cartridge carton 2600 and the cartridge receiving port 2705a of the stage rack 2700 are arranged so as to oppose each other. While they are opposing, the cartridges 112 and 114 are pushed from the cartridge push-out opening 2601c into the stage rack 2700 via the cartridge receiving port 2705a. The push-out mechanism 2520 including the push-out bar 2521 is omitted in FIG. 36. The position of the stage rack 2700 with respect to the cartridge carton 2600 shown in FIG. 36 is the cartridge supply position.

The stage rack 2700 is movable back and forth in the x-direction along the rail 2410 as shown in FIG. 36 by the stage rack transferring mechanism 2400. The first cartridge carton 2600 can be used to set the cartridges 112 into the plurality of lanes of the stage rack 2700. Once the cartridges 112 are set, the stage rack 2700 is moved in the x-direction, where the second cartridge carton 2600 (not shown) is used to set the cartridges 114 into the plurality of lanes of the stage rack 2700. While FIG. 36 only shows one cartridge carton 2600, a plurality of cartridge cartons 2600 are preferably arranged side by side as shown in FIG. 24.

Figure 37:
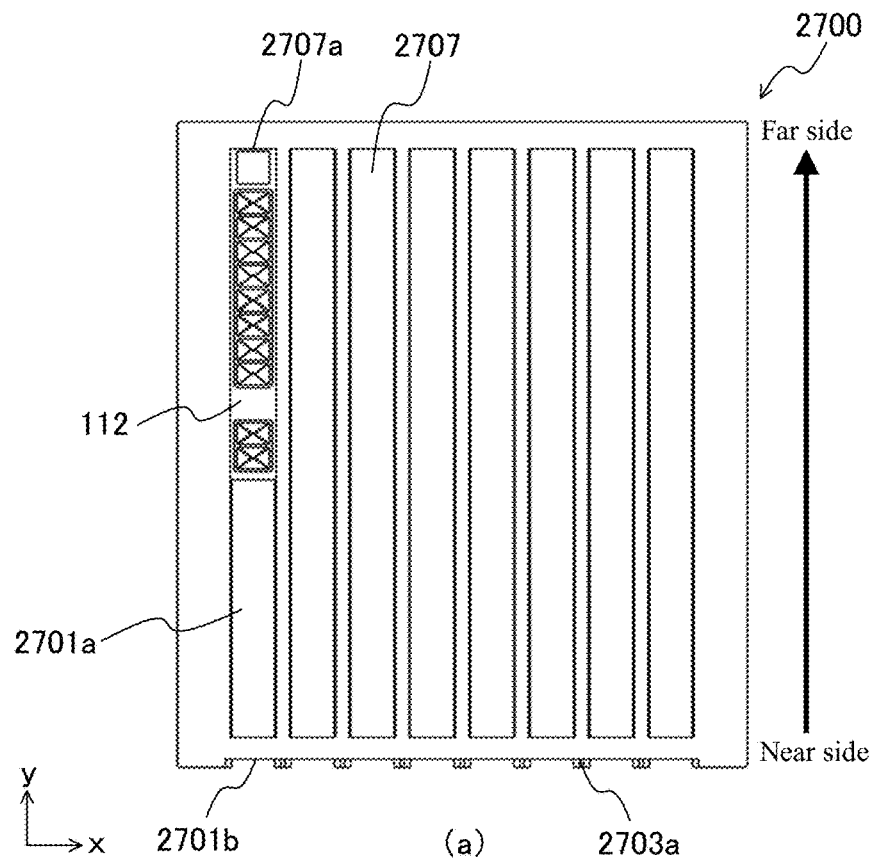
FIG. 37 A top view showing a state where the cartridge is inserted into the stage rack shown in FIG. 32.
Figure 37:
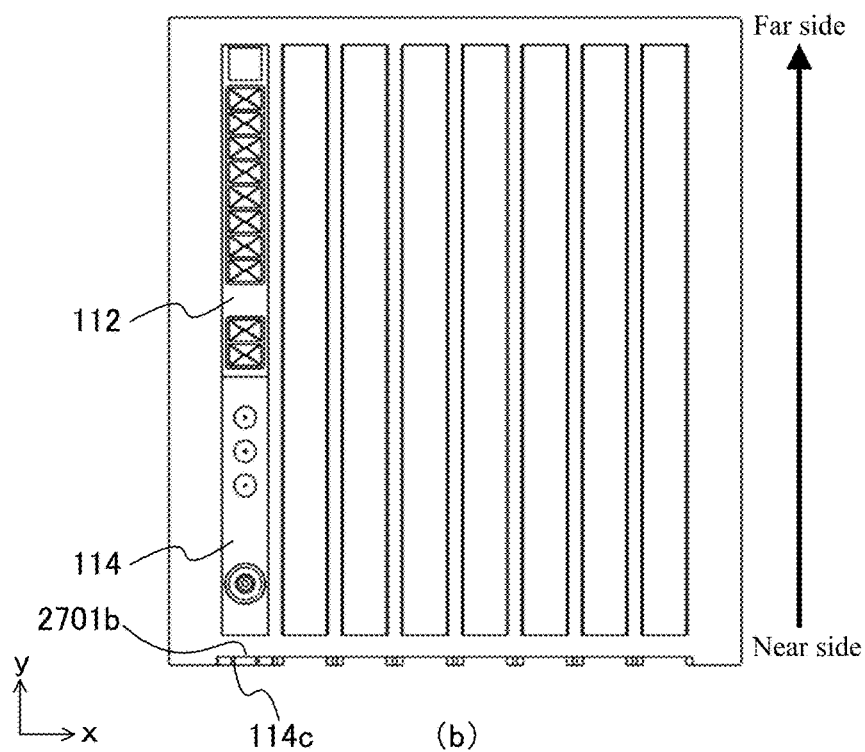

As shown in FIG. 37, the stage rack 2700 comprises a plurality of slim lanes (openings 2707), where each lane accommodates the plurality of cartridges 112 and 114 which form respective functional sections. For example, the stage rack 2700 can accommodate the DNA extraction cartridge 112 on the far side of the stage rack and the PCR cartridge 114 on the near side of the stage rack. The DNA extraction cartridge 112 forms an extraction functional section for extracting and purifying nucleic acids such as DNA from a specimen such as cells, whereas the PCR cartridge 114 forms a PCR and measurement functional section for executing PCR for the extracted DNA and measuring the DNA amplified by PCR. The end of the DNA extraction cartridge 112 on the far side is positioned to make contact with the inner surface 2707a of the opening 2707. The end of the PCR cartridge 114 on the near side is positioned such that the rib 114c of the PCR cartridge 114 abuts the outer side 2701b of the upper surface body 2701.

Figure 38:
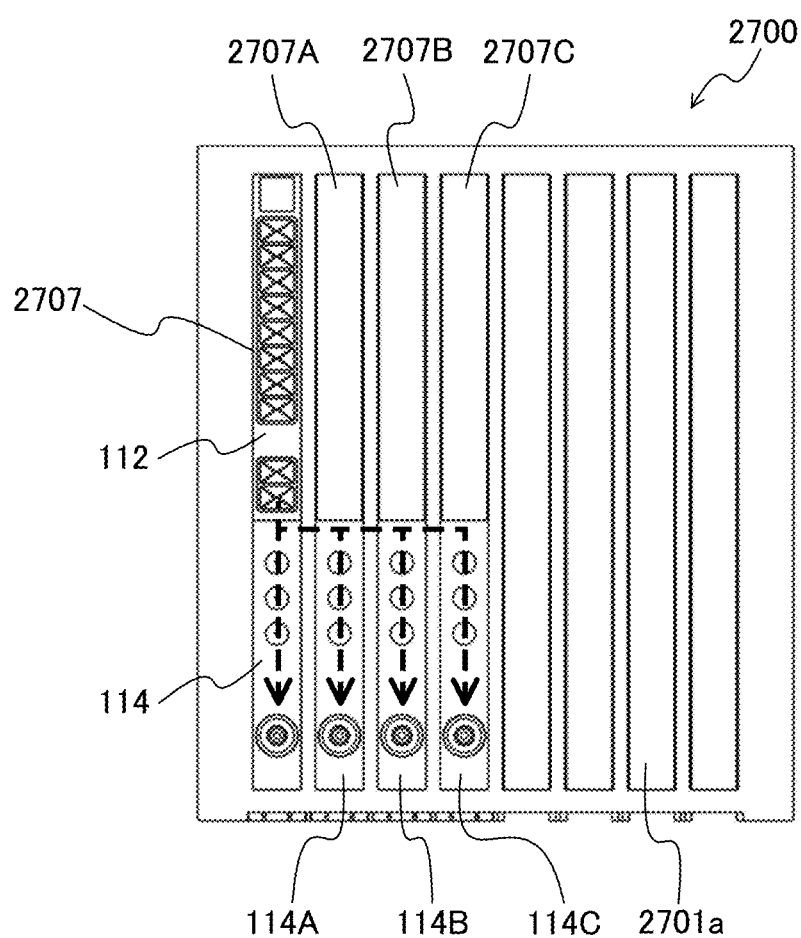
FIG. 38 A top view of the stage rack where a single specimen is measured for multiple items in the modified embodiment of the present invention.

FIG. 38 shows a state where the cartridges are set on the stage rack 2700 for measuring multiple items for a single specimen. In the cartridge supply module 2500, the DNA extraction cartridge 112 and the PCR cartridge 114 are set on the stage rack 2700 in advance as shown in FIG. 38. Specifically, one DNA extraction cartridge 112 and one PCR cartridge 114 are set into the first lane 2707, while one PCR cartridge 114A, 114B or 114C is set into the second to fourth lanes 2707A-2707C without the extraction cartridge 112. The stage rack 2700 in a state shown in FIG. 38 is transferred to the consumable supply module 2100 where the specimens, reagents and the like are dispensed, and then it is transferred the treatment execution module 2200 where extraction, PCR and a measurement of the specimen are executed.

In the treatment execution module 2200, after the specimen is extracted on the extraction cartridge 112 set into the first lane 2707, the stage rack 2700 is transferred to the consumable supply module 2100 again so as to dispense the extracted DNA from the extraction cartridge 112 into the PCR cartridges 114, 114A, 114B and 114C by using the dispenser nozzles 320 of the consumable supply module 2100. At the end of the dispensation into the PCR cartridges 114-114C, the stage rack 2700 is transferred to the treatment execution module 2200, where PCR and a measurement are executed on each of the PCR cartridges 114-114C. By supplying different reagents and else to the PCR cartridges 114-114C in advance, measurements for different items can be executed for a single specimen in parallel in the PCR cartridges 114-114C.

Figure 31:
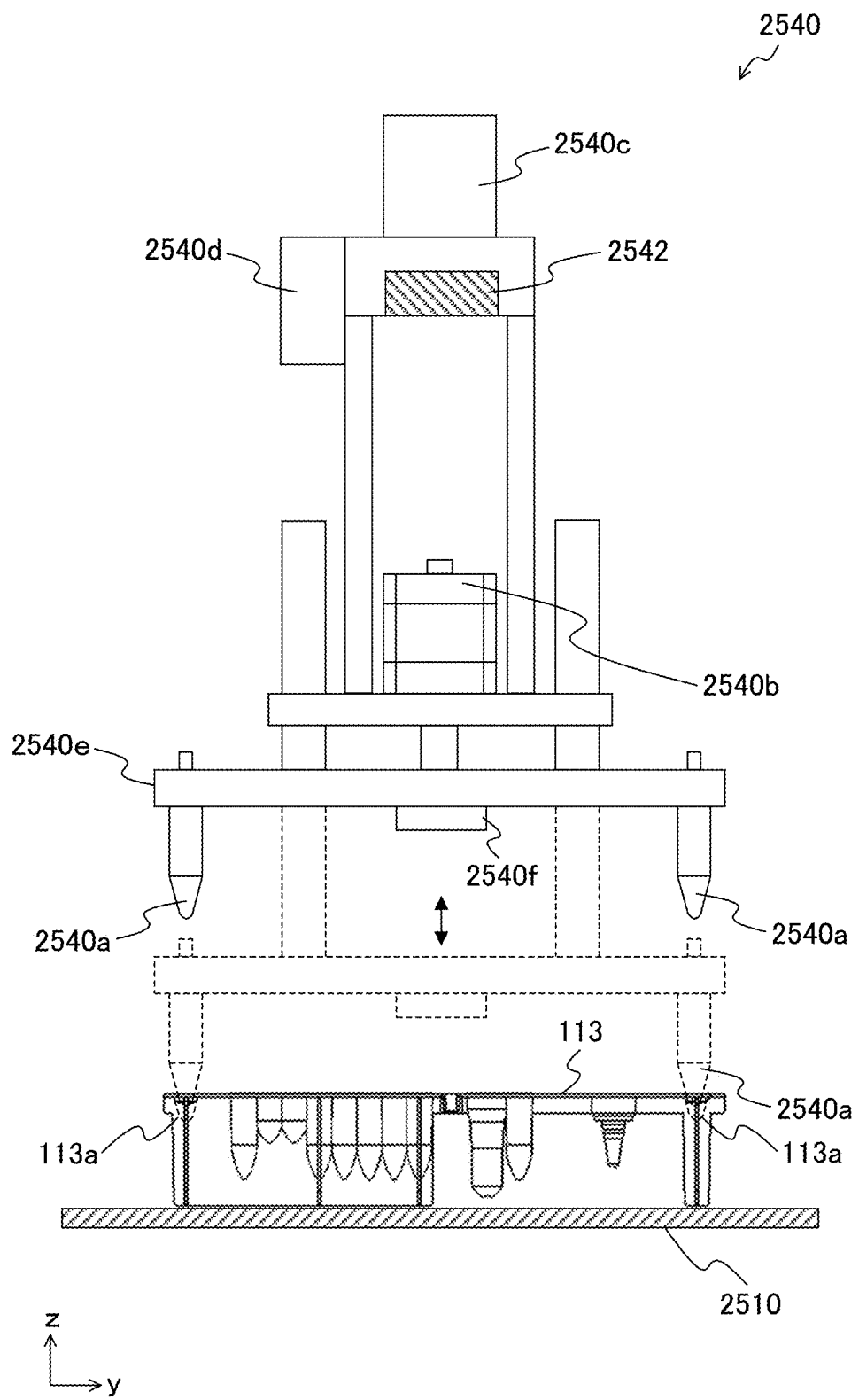
FIG. 31 A side view of a cartridge picker provided in the first embodiment of the present invention.

Since the cartridges can be set directly into the stage rack 2700 in the modified embodiment of the cartridge supply module (FIGS. 32-38), there is no need of the space for pushing out the cartridges onto the stage 2510, and no need of the cartridge picker shown in FIG. 31. In addition, according to this modified embodiment, the stage rack 2700 itself can hold the cartridges from the top and the bottom, and thus it does not require the mechanism for preventing floating of the cartridges as shown in FIGS. 17 and 18. Accordingly, in the modified embodiment, the structure of the cartridge supply module can be made compact and simple.

In the modified embodiment, the used cartridges are discarded from the stage rack 2700 by transferring the stage rack 2700 to the cartridge supply module 2500, where the cartridge may be pushed out from the far side to the near side in FIG. 37 by using the push-out mechanism (not shown) to be discarded in the discard box 2550. In the modified embodiment, two types of cartridges, namely, the DNA extraction cartridge 112 and the PCR cartridge 114, are used, but the present invention is not limited thereto, and a cartridge 113 in which the DNA extraction functional section and the PCR functional section are integrated may be used. The stage rack 2700 of the modified embodiment may have the structure similar to that of the stage racks 2300 shown in FIG. 10. For example, it may comprise one or any plurality of elements selected from a plurality of connection holes for transfer 2314, a plurality of connection holes for installation 2316, a tube accommodating part 2318 for accommodating specimen tubes, a plurality of partition walls 2312 for partitioning the lanes, and the plurality of partition walls 2313. Furthermore, the stage rack 2700 of the modified embodiment may comprise a cartridge securing mechanism for preventing the cartridge 114 from falling from the cartridge receiving port 2705a. This cartridge securing mechanism may be formed of, for example, a movable nail or the like for holding the edge of the cartridge on the cartridge receiving port 2705a side.

[Specimen Treatment and Measurement System According to Second Embodiment]

Figure 39:
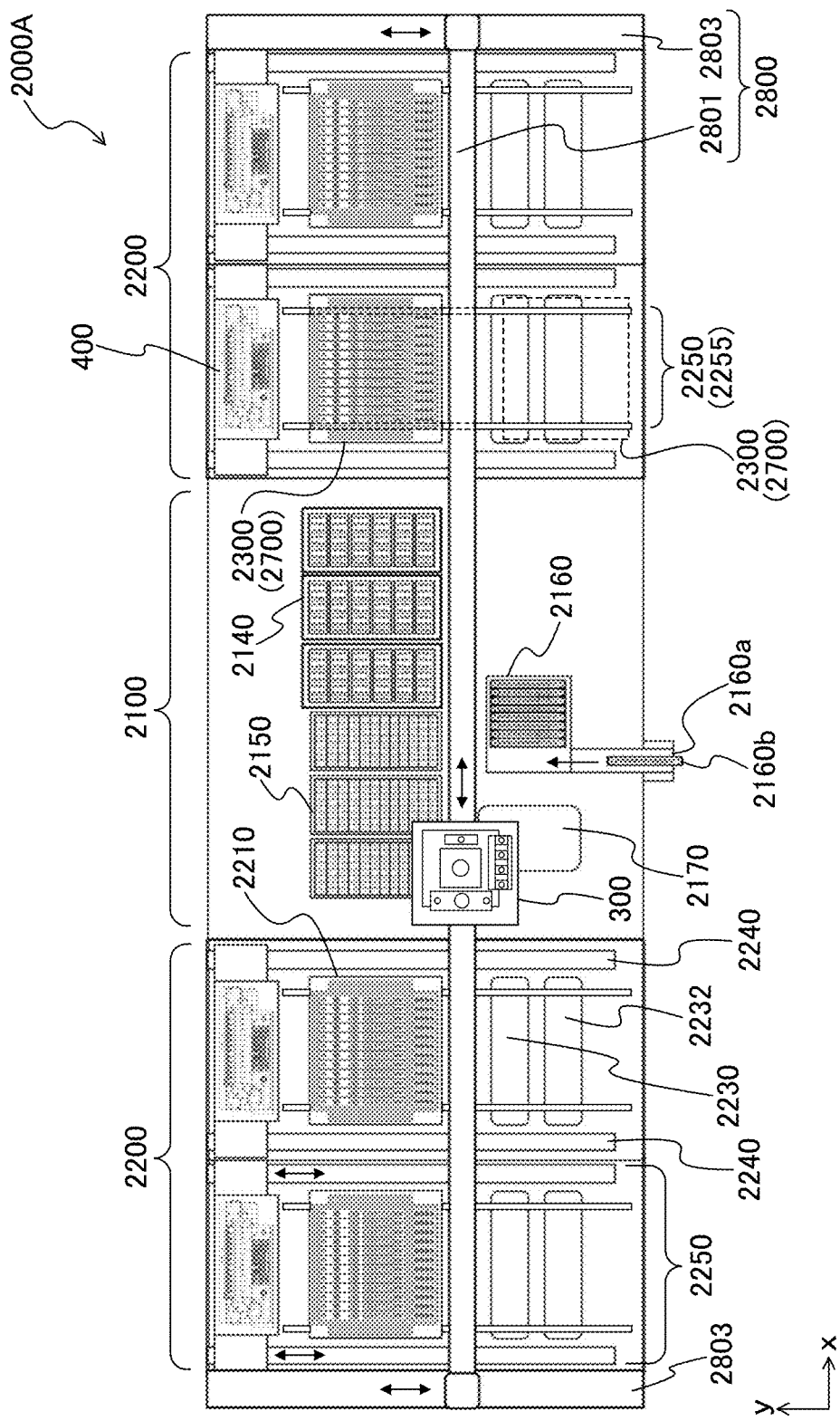
FIG. 39 A top view of a specimen treatment and measurement system according to a second embodiment of the present invention.

A specimen treatment and measurement system 2000A according to a second embodiment of the present invention will be described. As shown as the plan view in FIG. 39, the specimen treatment and measurement system 2000A comprises a consumable supply module 2100, one or a plurality of treatment execution modules 2200, one or the plurality of stage racks (movable stages) 2300 or 2700 detachable with respect to the one or a plurality of treatment execution modules 2200, a pick-up unit 300, and a pick-up unit moving mechanism 2800 for moving the pick-up unit 300 in a substantially horizontal way.

The pick-up unit 300 picks up or suctions a consumable, a specimen, a solution and/or a reagent from the consumable supply module 2100 and supplies them to a cartridge such as an integrated cartridge 113 that has been loaded on the stage rack 2300 or 2700. The pick-up unit moving mechanism 2800 comprises a first rail 2801 that allows the pick-up unit 300 to move back and forth in the x-direction, a x-direction movement motor (not shown) for moving the pick-up unit 300 in the x-direction along the first rail 2610, a pair of second rails 2803 that allow the first rail 2801 to move back and forth in the y-direction, and a y-direction movement motor (not shown) for moving the first rail 2803 in the y-direction. The pick-up unit 300 can be moved to arbitrary positions above each module by the pick-up unit moving mechanism 2800. The first rail 2801 of the pick-up unit moving mechanism 2800 is positioned to be higher than the treatment execution units 400 so that it does not interfere with the treatment execution units 400 that move in the y-direction. By positioning the first rail 2801 of the pick-up unit moving mechanism 2800 so as not to interfere with the treatment execution units 400, the pick-up unit 300 can supply a consumable, a specimen, a reagent, a solution and/or the like from the consumable supply module 2100 to one or the plurality of stage racks 2300 or 2700 installed in the treatment execution module 2200 shown in the right in FIG. 39, for example, while two treatment execution units 400 move in the y-direction in the treatment execution module 2200 shown in the left in FIG. 39 and execute a treatment (extraction, purification or amplification) or a measurement of the specimen.

The pick-up unit 300 moves across the consumable supply module 2100 and the plurality of treatment execution modules 2200. The specimen treatment and measurement system 2000A comprises the consumable supply module 2100 in the middle and the treatment execution modules 2200 on both sides of the consumable supply module 2100. In other words, the consumable supply module 2100 is arranged between the two treatment execution modules 2200. By this arrangement, the traveling distance of the pick-up unit 300 can be optimized. One of the treatment execution modules 2200 can comprise one or a plurality of treatment execution units 400. Although the specimen treatment and measurement system 2000A comprises two treatment execution modules 2200 in FIG. 39, it may alternatively comprise one treatment execution module 2200, or three or more treatment execution modules 2200.

The specimen treatment and measurement system 2000A according to the second embodiment does not comprise the cartridge supply module 2500 and the stage rack transferring mechanism 2400 according to the first embodiment. In the second embodiment, a plurality of integrated cartridges 113 are loaded in the respective treatment lanes of the stage rack 2300 or 2700 by the user while the stage rack 2300 or 2700 is at a cartridge loading position (not shown). The stage rack 2300 or 2700 on which the plurality of integrated cartridges 113 have been loaded is installed in the stage rack installing mechanism 2250 (FIGS. 11-15) by the user at an installation position in front of the treatment execution module 2200. Although use of the integrated cartridge 113 has been described in the second embodiment, the present invention is not limited thereto and a DNA extraction cartridge and a PCR cartridge may be arranged in a single treatment lane. The stage rack 2300 or 2700 installed in the stage rack installing mechanism 2250 moves in the y-direction by the stage rack installing mechanism 2250, and is installed in the stage rack installation section 2210.

[Summary]

Each of the embodiments of the present invention is characterized as follows.

(1) In the specimen treatment and measurement system 2000 of the first embodiment, the stage rack 2300 or 2700 in which a plurality of cartridges such as a plurality of integrated cartridges 113 have been installed can be automatically moved or exchanged. In the specimen treatment and measurement system 2000A of the second embodiment, the stage rack 2300 or 2700 in which a plurality of cartridges have been installed can be automatically moved or exchanged. Therefore, the specimen treatment and measurement systems according to the first and second embodiments can provide a configuration in which the stage rack 2300 or 2700 in which a plurality of cartridges have been installed can itself be exchanged (detached). Accordingly, the present invention is capable of continuously executing complicated treatment steps and measurement steps in parallel.

(2) The treatment execution modules 2200 of the first and second embodiments are capable of consistently and linearly performing extraction, amplification and fluorescence measurement of nucleic acids such as DNA in parallel for the plurality of cartridges loaded in the plurality of treatment lanes provided on the stage rack 2300 or 2700. The pick-up unit 300 of the first and second embodiments can automatically supply a specimen, a reagent, a solution and/or a consumable used for the reaction steps such as extraction, amplification and the like to the plurality of cartridges loaded on the stage rack 2300 or 2700.

(3) In the first and second embodiments, when a cartridge such as the integrated cartridge 113 is loaded on the stage rack 2300, the cartridge is secured onto the stage rack 2300 by the cartridge securing mechanism (FIGS. 16-18). Furthermore, in the first and second embodiment, when a cartridge is loaded on the stage rack 2700, the cartridge is slidably inserted into and secured to the stage rack 2700 via the cartridge receiving ports 2705a of the stage rack 2700. Accordingly, the cartridge at the installation position can be prevented from falling from the stage rack 2300 or 2700 when moving or exchanging the stage rack 2300 or 2700.

(4) In the treatment execution module 2200 of the first and second embodiments, the stage rack 2300 or 2700 loaded with a cartridge such as the integrated cartridge 113 is moved in the y-direction toward the stage rack installation section 2210, and halts at the stage rack installation section 2210. Then, the heat block (a heating/cooling unit such as a Peltier device) below the stage rack 2300 or 2700 moves up and down relative to the stage rack 2300 or 2700 by the elevating mechanism (not shown). As a result, the bottom surfaces of the plurality of amplification wells contained in the plurality of cartridges on the stage rack 2300 or 2700 make close contact with the heating/cooling unit. In this state, heat exchange upon PCR can take place efficiently.

(5) While installment of the cartridges into the stage rack 2300 or 2700 is not automated but operated by the user in the second embodiment, consumables, a specimen, a reagent, a solution and the like can automatically be supplied to the stage rack 2300 or 2700 by using the dispenser nozzles 320 of the pick-up unit (FIGS. 7 and 8). Accordingly, a partially automated random-batch-access system can be provided with a simpler configuration than the first embodiment

DESCRIPTION OF REFERENCE NUMERALS

300 Pick-up unit
400 Treatment execution unit (parallel treatment unit)
2000 Specimen treatment and measurement system
2000A Specimen treatment and measurement system
2100 Consumable supply module
2200 Treatment execution module
2300 Stage rack
2400 Stage rack transferring mechanism
2500 Cartridge supply module
2600 Cartridge carton
2700 Stage rack
2800 Pick-up unit moving mechanism

The invention claimed is:

1. A specimen treatment system for executing treatments including extraction, amplification and measurement of nucleic acids for multiple specimens in parallel, the system comprising:
a stage rack provided with a plurality of treatment lanes for executing the treatments in parallel;
a treatment execution module for executing the treatments by loading the stage rack therein;
a consumable supply module including a consumable supply stage for storing specimens and consumables used for the treatments, and a pick-up unit with joint ends jointed with openings of the consumables for picking up the consumables from the consumable supply stage; and
a cartridge supply module for storing cartridges that are used for at least one of extraction, amplification and measurement and supplying the cartridges to the stage rack, the cartridge supply module including a cartridge supply stage supplying the cartridges, and a cartridge picker for picking up one of the plurality of cartridges; and
a stage rack transfer mechanism for transferring the stage rack to each module, the stage rack transfer mechanism including at least one arm holding the stage rack, at least one rail movably holding the arm, and a transfer motor transferring the arm,
wherein the stage rack is detachable or exchangeable with respect to the treatment execution module, the stage rack having the plurality of cartridges disposed in the plurality of treatment lanes at the cartridge supply module,
wherein the treatment execution module comprises a treatment stage, a treatment execution unit having a plurality of dispensing nozzles and provided on the treatment stage, and the treatment execution unit executing measurement, a stage rack installation section installing the stage rack on the treatment stage, and a stage rack installing mechanism having a moving motor moving the stage rack to the stage rack installation section.

2. The specimen treatment system according to claim 1, wherein the treatment is a batch treatment that is performed for the multiple specimens at the same time.

3. The specimen treatment system according to claim 1, further comprising a second treatment execution module which is the same as the treatment execution module, wherein the consumable supply module is arranged between the treatment execution module and the second treatment execution module.

4. The specimen treatment system according to claim 1, wherein the cartridge supply module comprises at least one cartridge storage container for storing the cartridges in a stack, and a cartridge supplying mechanism for supplying the cartridges from the cartridge storage container to a supply position in the cartridge supply module.

5. The specimen treatment system according to claim 4, wherein the cartridge supplying mechanism supplies one cartridge in the bottommost row of the cartridges stacked in the cartridge storage container to the supply position.

6. The specimen treatment system according to claim 4, wherein the cartridge storage container and/or the cartridges comprise an information storage medium for readably storing the information of the cartridges.

7. The specimen treatment system according to claim 6, wherein the cartridge supply module comprises an information reading unit for reading cartridge information from the information storage medium.

8. The specimen treatment system according to claim 1, further comprising a cartridge securing mechanism for securing each of the cartridges to the stage rack, wherein the cartridge securing mechanism comprises a pin, a pin support, and a moving mechanism of the pin support, and the each of the cartridges has a recessed portion inserting the pin.

9. The specimen treatment system according to claim 1, wherein at least a part of each of the cartridges the cartridge comprises at least one prefilled well in which a solution used for the treatment, a reagent for extracting nucleic acids and/or a reagent for amplifying the nucleic acids is sealed in advance.

10. The specimen treatment system according to claim 1, wherein the stage rack comprises rails for slidably loading the cartridges, and cartridge receiving ports for accessing the cartridges to the rails.

11. The specimen treatment system according to claim 1, wherein the cartridges comprise a first cartridge and a second cartridge, where the first cartridge and the second cartridge are accommodated in one lane.

* * * * *